US012673155B2

(12) United States Patent
Pananen et al.

(10) Patent No.: US 12,673,155 B2
(45) Date of Patent: *Jul. 7, 2026

(54) INSERTION DEVICE WITH LINKAGE ASSEMBLY

(71) Applicant: MEDTRONIC MINIMED, INC., Northridge, CA (US)

(72) Inventors: Jacob E. Pananen, Agoura Hills, CA (US); Ellis Garai, Woodland Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 250 days.

This patent is subject to a terminal disclaimer.

(21) Appl. No.: 18/337,828

(22) Filed: Jun. 20, 2023

(65) Prior Publication Data

US 2023/0330331 A1 Oct. 19, 2023

Related U.S. Application Data

(63) Continuation of application No. 17/150,368, filed on Jan. 15, 2021, now Pat. No. 11,738,140.

(51) Int. Cl.
*A61M 5/158* (2006.01)
*A61M 5/172* (2006.01)

(52) U.S. Cl.
CPC .......... *A61M 5/158* (2013.01); *A61M 5/1723* (2013.01); *A61M 2005/1585* (2013.01); *A61M 2230/201* (2013.01)

(58) Field of Classification Search
CPC .. A61M 5/158; A61M 5/1723; A61M 5/3287; A61M 2005/1585;
(Continued)

(56) References Cited

U.S. PATENT DOCUMENTS 5,586,553 A * 12/1996 Halili ................... A61B 5/6849
600/377
6,364,865 B1 * 4/2002 Lavi .................... A61M 5/2448
604/411
(Continued)

FOREIGN PATENT DOCUMENTS

CA 3052310 A1 9/2018
CA 3143537 A1 12/2020
(Continued)

*Primary Examiner* — Bhisma Mehta
*Assistant Examiner* — Adam J. Cermak
(74) *Attorney, Agent, or Firm* — Fortem IP LLP

(57) ABSTRACT

An insertion device configured to implant a first medical device and a second medical device in a user. The first medical device may be a fluid delivery cannula configured to deliver a fluid (e.g., insulin) to the user. The second medical device may be an analyte sensor (e.g., a glucose sensor) configured to detect a physiological characteristic of the user (e.g., a glucose level). The insertion device may be configured to be worn by the user. The insertion device includes a first linkage assembly configured to extend and retract a first insertion needle to implant the first medical device and a second linkage assembly configured to extend and retract a second insertion needle to implant the second medical device. The insertion device includes a user input device configured to cause the insertion device to initiate the implantation when activated by the user.

20 Claims, 6 Drawing Sheets

(58) Field of Classification Search

CPC .. A61M 2005/14252; A61M 2230/201; A61B 5/14503; A61B 5/14532

See application file for complete search history.

(56) References Cited

U.S. PATENT DOCUMENTS

| | | | | |
|---|---|---|---|---|
| 8,641,670 | B2 | 2/2014 | Yodfat et al. | |
| 8,679,062 | B2 | 3/2014 | Yodfat et al. | |
| 8,747,363 | B2 | 6/2014 | Nielsen et al. | |
| 8,821,442 | B2* | 9/2014 | Haar | A61M 5/14248 320/128 |
| 8,998,851 | B2* | 4/2015 | Constantineau | A61M 5/158 604/136 |
| 9,545,477 | B2 | 1/2017 | Chong et al. | |
| 9,610,402 | B2* | 4/2017 | Yavorsky | A61M 5/142 |
| 9,764,124 | B2 | 9/2017 | Tallarida et al. | |
| 9,839,747 | B2 | 12/2017 | Smith et al. | |
| 9,943,643 | B2* | 4/2018 | Constantineau | A61B 17/3415 |
| 10,076,605 | B2* | 9/2018 | Marbet | A61M 5/14248 |
| 10,092,691 | B2 | 10/2018 | Searle et al. | |
| 10,195,342 | B2 | 2/2019 | Cole et al. | |
| 10,220,145 | B2 | 3/2019 | Jennewine | |
| 10,413,183 | B2 | 9/2019 | Antonio et al. | |
| 10,413,658 | B2 | 9/2019 | Gillett et al. | |
| 10,441,717 | B2* | 10/2019 | Schmid | A61M 5/14248 |
| 10,463,787 | B2* | 11/2019 | Shor | A61J 1/2003 |
| 10,569,011 | B2 | 2/2020 | Dilanni et al. | |
| 10,596,295 | B2 | 3/2020 | Larson et al. | |
| 11,241,532 | B2* | 2/2022 | Nazzaro | A61M 5/14248 |
| 11,738,140 | B2* | 8/2023 | Pananen | A61M 5/3287 604/504 |
| 2004/0010207 | A1* | 1/2004 | Flaherty | A61B 5/157 600/573 |
| 2004/0162521 | A1* | 8/2004 | Bengtsson | A61B 5/1518 604/173 |
| 2006/0253085 | A1 | 11/2006 | Geismar et al. | |
| 2007/0016129 | A1* | 1/2007 | Liniger | A61M 5/158 604/93.01 |
| 2007/0191702 | A1 | 8/2007 | Yodfat et al. | |
| 2007/0219597 | A1 | 9/2007 | Kamen et al. | |
| 2008/0051718 | A1 | 2/2008 | Kavazov et al. | |
| 2008/0195045 | A1* | 8/2008 | Lanigan | A61B 5/150358 604/117 |
| 2008/0208139 | A1* | 8/2008 | Scheurer | A61M 5/158 604/192 |
| 2009/0012472 | A1 | 1/2009 | Ahm et al. | |
| 2009/0062767 | A1* | 3/2009 | Van Antwerp | A61B 5/6849 600/316 |
| 2010/0051716 | A1 | 3/2010 | Walton | |
| 2010/0152674 | A1* | 6/2010 | Kavazov | A61M 5/1413 604/218 |
| 2011/0040160 | A1* | 2/2011 | Sakata | A61B 5/1486 600/309 |
| 2011/0152717 | A1* | 6/2011 | Kim | A61B 10/0233 600/568 |
| 2011/0251624 | A1* | 10/2011 | Yi | A61B 17/3403 606/130 |
| 2012/0109062 | A1* | 5/2012 | Lanigan | A61B 5/150503 604/164.12 |
| 2012/0245536 | A1 | 9/2012 | Gerber et al. | |
| 2012/0265042 | A1* | 10/2012 | Neinast | A61B 17/3468 600/347 |
| 2012/0265166 | A1* | 10/2012 | Yodfat | A61M 5/1413 604/151 |
| 2014/0031793 | A1* | 1/2014 | Constantineau | A61M 5/14248 604/164.12 |
| 2014/0148784 | A1* | 5/2014 | Anderson | A61M 5/14248 604/150 |
| 2015/0141776 | A1* | 5/2015 | Hadvary | A61B 5/14503 604/173 |
| 2015/0164545 | A1* | 6/2015 | Gyrn | A61M 5/158 600/300 |
| 2015/0290391 | A1* | 10/2015 | Schmid | A61M 5/14248 604/504 |
| 2016/0199590 | A1* | 7/2016 | Schabbach | A61M 5/34 604/240 |
| 2016/0213839 | A1* | 7/2016 | Schabbach | A61M 5/158 |
| 2016/0250422 | A1* | 9/2016 | Koch | A61M 5/1424 604/110 |
| 2017/0021137 | A1 | 1/2017 | Cole | |
| 2017/0112534 | A1* | 4/2017 | Schoonmaker | A61B 17/3468 |
| 2017/0232191 | A1 | 8/2017 | Smith et al. | |
| 2018/0368774 | A1* | 12/2018 | Gray | A61B 5/6848 |
| 2019/0160225 | A1* | 5/2019 | Verlaak | A61M 5/14248 |
| 2020/0023122 | A1 | 1/2020 | Mccullough et al. | |
| 2020/0069875 | A1* | 3/2020 | Nazzaro | A61M 5/1723 |
| 2020/0254172 | A1* | 8/2020 | Forster | A61M 5/142 |
| 2020/0261658 | A1* | 8/2020 | Farris | A61M 5/14248 |
| 2020/0384193 | A1 | 12/2020 | Chiu et al. | |
| 2022/0105267 | A1* | 4/2022 | Cardinali | A61M 5/1723 |
| 2022/0168502 | A1* | 6/2022 | Pananen | A61M 5/14248 |
| 2022/0226567 | A1 | 7/2022 | Pananen et al. | |
| 2022/0226573 | A1* | 7/2022 | Pananen | A61B 5/6848 |

FOREIGN PATENT DOCUMENTS

| | | |
|---|---|---|
| CN | 101027094 A | 8/2007 |
| CN | 102573810 A | 7/2012 |
| CN | 107405446 A | 11/2017 |
| EP | 3260151 A1 | 12/2017 |
| EP | 3354303 A1 | 8/2018 |
| WO | 2017219155 A1 | 12/2017 |

* cited by examiner

240

ROTATING A FIRST LINKAGE
ASSEMBLY AND A SECOND
LINKGAGE ASSEMBLY

242

EXTENDING A FIRST
INSERTION NEEDLE AND A
SECOND INSERTION NEEDLE

244

IMPLANTING A FIRST
MEDICAL DEVICE AND A
SECOND MEDICAL DEVICE

INSERTION DEVICE WITH LINKAGE ASSEMBLY

CROSS-REFERENCE TO RELATED APPLICATIONS

This application is a continuation of U.S. application Ser. No. 17/150,368, filed Jan. 15, 2021, which is incorporated herein by reference in its entirety.

TECHNICAL FIELD

This disclosure relates generally to systems for the insertion of medical devices.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is often treated by delivering defined amounts of insulin to the patient at appropriate times. Some modern systems employ programmable fluid infusion devices (e.g., insulin pumps) to deliver controlled amounts of insulin to a patient. Some modes of providing insulin therapy to a user include delivery of insulin through manually operated syringes and insulin pens. Some other modes employ programmable fluid infusion devices (e.g., insulin pumps) to deliver controlled amounts of insulin to a user. Moreover, in certain instances, it may be desirable for a user to receive feedback from a physiological characteristic monitor, such as a glucose monitor. In these instances, the physiological characteristic monitor and the infusion set are often separately coupled to the user's anatomy at different insertion sites.

BRIEF SUMMARY

The disclosure generally relates to an insertion device for implanting a first medical device and a second medical device within a user. The insertion device may be configured to be worn by the user, and may include a housing configured to contact the skin of the user. The insertion device includes a first insertion needle and a second insertion needle configured to implant the first medical device and the second medical device by extending from the housing and releasing the devices. The insertion device is configured to retract the first insertion needle and the second insertion needle back into the housing while the first medical device and the second medical device remain implanted.

In examples, the first medical device is a fluid delivery cannula configured to deliver a fluid (e.g., insulin) from a fluid reservoir to the user. In examples, the second medical device is an analyte sensor (e.g., a glucose sensor) configured to provide a signal indicative of a physiological characteristic of the user (e.g., a glucose level). The insertion device may include a fluid pump configured to cause the fluid delivery cannula to deliver the fluid, and may include processing circuitry configured to receive the signal indicative of the physiological characteristic and determine the physiological characteristic. In examples, the processing circuitry is configured to control the operation of the fluid pump based on the indicative signal.

In an example, an insertion device for insertion of a first medical device and a second medical device into a user comprises: a housing; a first insertion needle configured to pierce and withdraw from skin of the user, the first insertion needle configured to releasably carry the first medical device; a second insertion needle configured to pierce and withdraw from the skin, the second insertion needle configured to releasably carry the second medical device; a first linkage assembly within the housing; a second linkage assembly within the housing; and a driver within the housing configured to cause the first linkage assembly and the second linkage assembly to rotate relative to the housing, wherein the first linkage assembly is configured to cause the first insertion needle to extend in a first direction away from the housing to pierce the skin and subsequently retract toward the housing to withdraw from the skin when the driver causes the first linkage assembly to rotate relative to the housing, and wherein the second linkage assembly is configured to cause the second insertion needle to extend in a second direction away from the housing to pierce the skin and subsequently retract toward the housing to withdraw from the skin when the driver causes the second linkage assembly to rotate relative to the housing.

In an example, an insertion device for insertion of a first medical device and a second medical device into a user comprises: a housing; a first insertion needle configured to pierce and withdraw from skin of the user at a first location, the first insertion needle configured to releasably carry the first medical device; a second insertion needle configured to pierce and withdraw from skin of the user at a second location displaced from the first location, the second insertion needle configured to releasably carry the second medical device; a first linkage assembly within the housing; a second linkage assembly within the housing; and a driver configured to concurrently cause the first linkage assembly and the second linkage assembly to rotate relative to the housing, wherein: the first linkage assembly is configured to cause the first insertion needle to extend in a first direction away from the housing to pierce the skin and subsequently retract toward the housing to withdraw from the skin when the first linkage rotates relative to the housing, the first insertion needle is configured to release the first medical device when the first insertion needle retracts toward the housing, the second linkage assembly is configured to cause the second insertion needle to extend in a second direction away from the housing to pierce the skin and subsequently retract toward the housing to withdraw from the skin when the second linkage rotates relative to the housing, and the second insertion needle is configured to release the second medical device when the second insertion needle retracts toward the housing.

In an example, a technique includes: extending a first insertion needle of the insertion device in a first direction away from a housing to pierce skin using rotation of a first linkage assembly with respect to the housing, wherein the first insertion needle is configured to releasably carry a first medical device; extending a second insertion needle of the insertion device in a second direction away from the housing to pierce the skin using rotation of a second linkage assembly with respect to the housing, wherein the second insertion needle is configured to releasably carry a second medical device; retracting the first insertion needle toward the housing to withdraw from the skin using the rotation of the first linkage assembly; and retracting the second insertion needle toward the housing to withdraw from the skin using the rotation of the second linkage assembly.

The details of one or more examples are set forth in the accompanying drawings and the description below. Other features, objects, and advantages will be apparent from the description and drawings, and from the claims.

DETAILED DESCRIPTION

Figure 1:
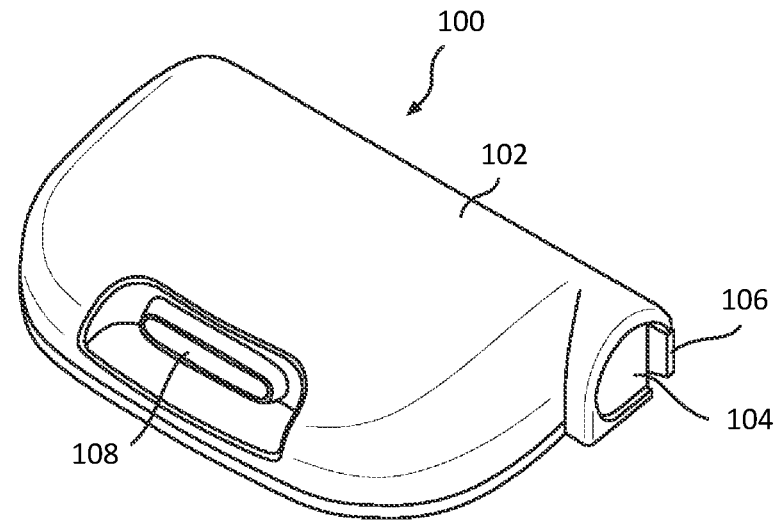
FIG. 1 is a top perspective view of an example of an insertion device.

The disclosure describes an insertion device configured to implant a first medical device and a second medical device within a patient. The insertion device may be generally related to a fluid infusion device configured to provide a therapeutic fluid to a user and monitor a physiological characteristic of the user. For example, the first medical device may be a fluid delivery cannula configured to deliver a fluid (e.g., insulin) to the user. The second medical device may be an analyte sensor (e.g., a glucose sensor) configured to detect a physiological characteristic of the user (e.g., a glucose level). The insertion device may be configured to insert the first medical device and the second medical device in the user substantially concurrently. In examples, the insertion device is a portable device configured to be worn by the user.

The insertion device includes a housing configured to position the insertion device proximate to the skin of the user. In examples, the housing is configured to contact the skin of the user. The housing may be configured to substantially secure its location on the user in order to, for example, allow mobility to the user as the insertion device administers and monitors therapies delivered to the user. For example, the insertion device may be configured to allow a degree of user mobility as the insertion device delivers insulin to the user through a fluid delivery cannula (e.g., the first medical device) and monitors a glucose level of the user using an analyte sensor (e.g., the second medical device). The insertion device may be substantially secured to the user using any suitable arrangement. In some examples, the housing of the insertion device includes an adhesive element configured to removably secure the housing to the skin of the user.

In examples, the insertion device is configured such that, when positioned on the skin of the user, the user may initiate the implantation of the first medical device and the second medical device. For example, the user may initiate the implantation using a manually operated button on the housing, a wireless communication to the medical system, or some other user-controlled activation. The insertion device is configured to cause a first insertion needle and a second insertion needle to extend to implant the first and second medical devices, and configured to subsequently withdraw the insertion needles from the user as the first and second medical devices remain implanted within the user. In examples, the housing mechanically supports an insertion mechanism unit including the first and second insertion needles, and the housing may be detached from the insertion device following implantation in order to, for example, reduce an overall volume and/or profile of the insertion device to lessen burden on the user.

The first and second insertion needles are configured to pierce and withdraw from the skin of the user. Upon activation by the user, the insertion device causes the first insertion needle and the second insertion needle to extend from the housing to pierce the skin and to subsequently retract toward the housing to withdraw from the skin. The first insertion needle is configured to releasably carry the first medical device, such that the first insertion needle substantially implants the first medical device during its extension and leaves the first medical device implanted within the user during its retraction. The second insertion needle is configured to releasably carry the second medical device, such that the second insertion needle substantially implants the second medical device during its extension and leaves the second medical device implanted during its retraction. In examples, the insertion device is configured to cause the first and second insertion needles to cause implantation of the first medical device and second medical device substantially concurrently. The substantially concurrent insertion of the first insertion needle and the second insertion needle insert may, for example, limit discomfort to the user that might be caused by insertions separated by a user-discernable chronological time increment. In examples, the insertion device is configured to cause the first and second insertion needles to withdraw substantially concurrently in order to, for example, limit discomfort to the user that might be caused by withdrawals separated by a user-discernable chronological time increment.

The insertion device may be configured to cause the first insertion needle to extend in a first direction away from the housing and cause the second insertion needle to extend in a different, second direction away from the housing, in order to implant the first medical device at a location displaced from the second medical device. The displacement may reduce negative effects that may occur due to a proximity between the first medical device and the second medical devices once implanted. For example, the insertion device may be configured to implant a fluid delivery cannula at a first location and implant an analyte sensor at a second location displaced from the first location, such that readings reported by the analyte sensor (e.g., glucose levels) are not adversely impacted by delivery of a fluid (e.g., insulin) through the fluid delivery cannula.

The insertion device may include a variety of internal components configured to use the first medical device and the second medical device to provide therapy and monitor a physiological characteristic of the user. In examples, at least one of the first medical device or the second medical device is a fluid delivery cannula, and the insertion device includes a fluid pump (e.g., an insulin pump) configured to deliver a fluid (e.g., insulin) to the user from a fluid reservoir within the medical system. The fluid reservoir may be, for example, a volume defined by a detachable fluid cartridge configured to mechanically engage a housing of the insertion device to establish fluid communication with the fluid pump. In examples, the insertion device includes processing circuitry configured to control an operation of the fluid pump. For example, the processing circuitry may be configured to cause the fluid pump to commence, continue, and/or cease transporting fluid from the fluid reservoir through the fluid delivery cannula. In examples, at least one of the first medical device or the second medical device is an analyte sensor configured to generate a signal indicative of a physiological characteristic of the user (e.g., a glucose level), and the processing circuitry is configured to determine the physiological characteristic using the indicative signal. In some examples, the processing circuitry is configured to control an operation of the fluid pump based on the indicative signal reported by the analyte sensor.

The insertion device includes a first linkage assembly configured to control the motion of the first insertion needle and a second linkage assembly mechanism configured to control the motion of the second insertion needle. The insertion device includes a driver configured to cause a rotation of the first linkage assembly and the second linkage assembly relative to the housing to control the motion of the first insertion needle and second insertion needle respectively. The driver may be configured to cause the rotation of the first linkage assembly and the second linkage assembly substantially concurrently, such that the first insertion needle and the second insertion needle extend away from the housing and retract toward the housing substantially concurrently.

The first linkage assembly linkage assembly includes a first plurality of interconnected links (e.g., elongated bodies), including a first input link and a first output link. The first plurality of interconnected links defines a first kinematic chain, such that rotation of the first input link relative to the housing causes movement of the first output link relative to the housing and relative to the first input link. The rotation of the first linkage assembly (e.g., the input link) causes the first linkage assembly (e.g., a first output link) to extend and retract the first insertion needle. The first linkage assembly may include one or more floating links in the first kinematic chain defined by the first input link and the second output link.

In some examples, the first output link is configured to linearly translate (e.g., experience a sliding stroke) when the driver rotates the first input link. The first output link may be constrained to slide within a channel defined by the insertion device (e.g., defined by the housing). In examples, the first linkage assembly is configured such that a rotation of the first input link in a single direction causes the first output link to initially linearly translate in a first direction and subsequently linearly translate in a second direction opposite the first direction. The first output link is configured to cause the first insertion needle to implant the first medical device when moving in the first direction, and subsequently withdraw the first insertion needle when moving in the second direction.

The second linkage assembly may include a second plurality of links defining a second kinematic chain. The second plurality of links may be configured similarly to the first linkage assembly. For example, the second linkage assembly may include a second input link and a second output link, where a rotation of the second input link relative to the housing causes the second output link to linearly translate. The linear translation of the second output link may cause the second insertion needle to extend away from the housing to implant the second medical device and subsequently retract toward the housing.

The driver may be configured to cause the rotation of the first linkage assembly (e.g., the first input link) and second linkage assembly (e.g., the second input link) substantially concurrently when the user activates the insertion device for implantation. For example, the driver may include a wound torsion spring configured to substantially unwind when the user activates the medical system. In examples, the housing defines a central axis, and the driver is configured to cause the first input link of the first linkage assembly and the second input link of the second linkage assembly to rotate around the central axis and relative to the housing. In some examples, the torsion spring surrounds the central axis, and the first input link and the second input link are coupled to respective ends of the torsion spring such that an unwinding of the torsion spring causes the first input link and second input link to rotate relative to the housing in substantially opposite directions. In some examples, the driver includes a hub configured to rotate around the central axis, and the first input link and the second input link are coupled to the hub such that rotation of the hub causes the first input link and second input link to rotate relative to the housing in the same direction. The hub may rotate due to an unwinding of the torsion spring, or by the action of some other suitable mechanism configured to generate a torque on the hub.

Hence, the insertion device may be configured to position proximate the skin of a user and cause a first insertion needle and a second insertion needle to extend away from the housing to pierce the skin and retract toward the housing to withdraw from the skin. The first insertion needle may be configured to implant a first medical device in the user and the second insertion needle may be configured to implant a second medical device in the user. The insertion device may include a user input device configured to allow the user to control when the insertion device causes the implantation of the first medical device and the second medical device. In examples, the first medical device is a fluid delivery cannula and the second medical device is an analyte sensor. The insertion device may include a fluid pump (e.g., an insulin pump) configured to deliver a fluid (e.g., insulin) to the user, and may include processing circuitry configured to receive signals indicative of a physiological characteristic of the user (e.g., a glucose level) from the analyte sensor. The processing circuitry may be configured to control an operation of the fluid pump based on the indicative signals received from the analyte sensor. The insertion device may be utilized to administer a variety of medications to a user such as, but not limited to, disease treatments, drugs to treat pulmonary hypertension, iron chelation drugs, pain medications, anti-cancer treatments, medications, vitamins, hormones, or the like.

Figure 2:
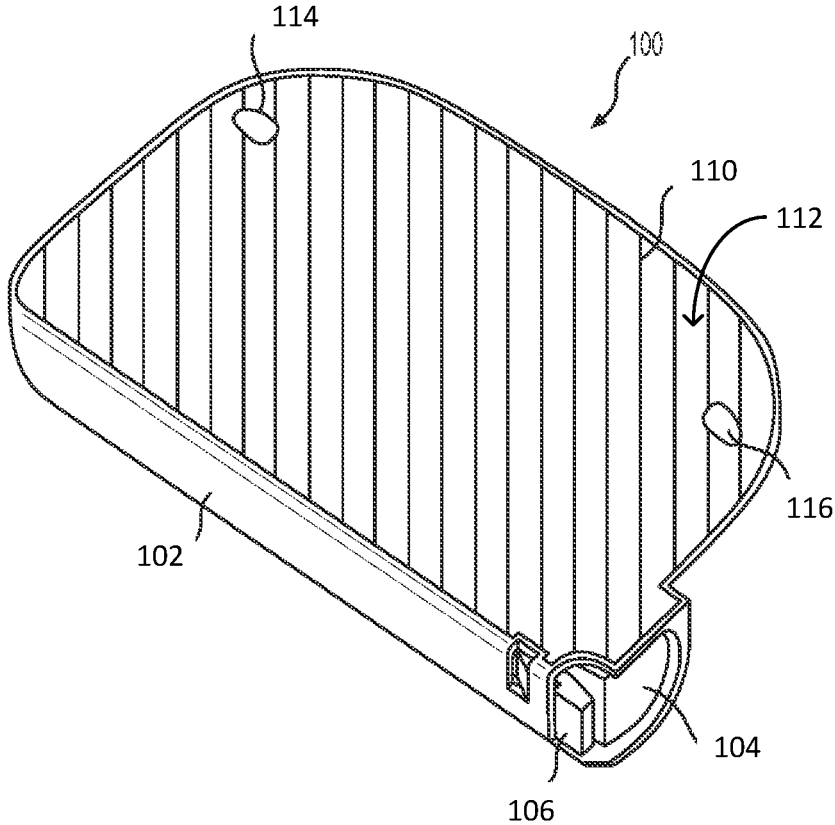
FIG. 2 is a bottom perspective view of the insertion device of FIG. 1.
Figure 3:
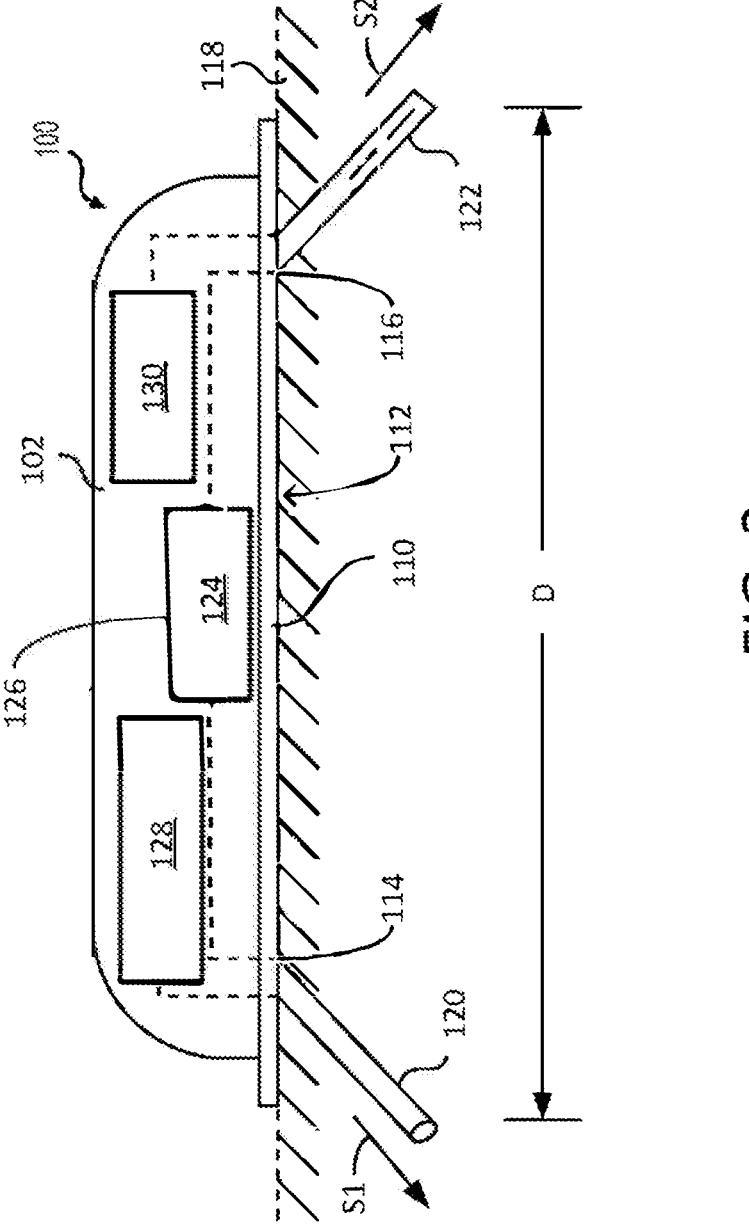
FIG. 3 is a schematic side view of an insertion device attached to the body of a user.

FIG. 1 is a top perspective view of an example of an insertion device 100 configured as a fluid infusion device. The fluid infusion device may be implemented as a patch pump device (e.g., worn on the stomach or on the arm). FIG. 2 is a bottom perspective view of insertion device 100. FIG. 3 is a schematic side view of insertion device 100 contacting the body of a user. FIGS. 1, 2, and 3 depict one possible configuration and form factor of insertion device 100. Other designs and configurations can be utilized if so desired, and the particular design aspects shown and/or described in FIGS. 1, 2, 3, and elsewhere are not intended to limit or otherwise restrict the scope or application of the examples described herein.

Insertion device 100 includes a device housing 102 that may serve as a shell for a variety of internal components of insertion device 100. For example, device housing 102 may mechanically support one or more internal components configured to monitor a physiological characteristic of a user and/or delivery therapy to the user. In examples, device housing 102 is configured to mechanically support one or more insertion needles configured to implant one or more medical devices into the user. Device housing 102 may mechanically support components configured to cause the one or more insertion needles to implant the medical devices in the user. In some examples, device housing 102 is configured to mechanically support internal components configured to utilize and/or communicate with the medical devices for monitoring of and/or delivering therapy to the user. For example, device housing 102 may mechanically support a first insertion needle configured to implant a fluid delivery cannula into the user, a second insertion needle configured to implant an analyte sensor into the user, a fluid pump configured to deliver a fluid from a fluid reservoir using the fluid delivery cannula, and processing circuitry configured to communicate with the analyte sensor and/or the fluid pump. Device housing 102 may be configured to position insertion device 100 proximate and/or in contact with the skin of the user.

In examples, device housing 102 may be configured to mechanically support a removable fluid cartridge 104 defining a fluid reservoir. Fluid cartridge 104 may be, for example, a disposable insulin cartridge. Device housing 102 may be suitably configured to receive, secure, and release fluid cartridge 104. For example, FIG. 1 and FIG. 2 depict a fluid cartridge 104 installed on and substantially secured by device housing 102. Device housing 102 may be configured such that, when fluid cartridge 104 is mechanically supported by (e.g., installed on) device housing 102, a fluid pump mechanically supported by device housing 102 establishes fluid communication with the fluid reservoir defined by fluid cartridge 104. Device housing 102 may include a suitably shaped, sized, and configured cavity configured to engage particular physical characteristics of fluid cartridge 104. For example, the device housing 102 can include structural features that mate with or otherwise engage structural features of fluid cartridge 104.

Fluid cartridge 104 may have any shape, size, and/or configuration sufficient to engage with device housing 102. In examples, fluid cartridge 104 includes a cartridge retention mechanism 106 configured to secure fluid cartridge 104 in an installed and seated position within insertion device 100. Retention mechanism 106 may mechanically engage device housing 102 to substantially lock the fluid cartridge 104 in place to maintain physical and fluid connections between the fluid cartridge 104 and insertion device 100. Retention mechanism 106 may be configured to allow physical manipulation by the user to release and/or install fluid cartridge 104 on device housing 102 as needed.

Insertion device 100 includes at least one user input device 108 which may be actuated by the user as needed. User input device 108 may be a manually operated button on device housing 102, a circuitry configured to receive a communication (e.g., a wireless communication) from a smart phone, tablet, or other device, or some other device configured for control by the user. In examples, user input device 108 (e.g., a button) is configured to cause insertion device 100 to implant a first medical device and/or second medical device into the user. However, the user input device 108 may be a multipurpose user interface configured to prompt multiple operations of insertion device 100. For example, user input device 108 may be configured to cause one or more of the following functions, without limitation: waking up the processor and/or electronics of insertion device 100; triggering an insertion mechanism unit to implant a first medical device (e.g., a fluid delivery cannula) and/or a second medical device (e.g., an analyte sensor) into a subcutaneous space or similar region of the user; configuring one or more settings of insertion device 100; initiating delivery of medication fluid; initiating a fluid priming operation; disabling alerts or alarms generated by insertion device 100; and the like. In lieu of or in addition to a button, user input device 108 can employ a slider mechanism, a pin, a lever, a switch, a touch-sensitive element, or the like.

User input device 108 may be configured to receive a communication from a device remote from device housing 102 (e.g., a wireless communication) to initiate insertion device 100 to perform one or more of the described functions, or other functions. In examples, insertion device 100 includes more than one user input device 108 (e.g., more than one button) to initiate the various functions described.

In examples, insertion device 100 is a portable device. Insertion device 100 may be a wearable device configured to be worn by the user. As depicted in FIG. 2, insertion device 100 may include an adhesive element 110 or an adhesive material configured to substantially affix the device housing 102 to the body of the user. Adhesive element 110 may be configured to substantially secure insertion device 100 in a location proximate (e.g., contacting) the skin 118 (FIG. 3) of the user. Adhesive element 110 may be located on a bottom surface of the device housing 102 such that the device housing 102 can be temporarily adhered to the skin of the user. The adhesive element 110 may cover substantially all of the lower surface (as depicted), or it can only partially cover the lower surface if so desired. Adhesive element 110 may be, for example, a piece of double sided adhesive tape that is cut into the desired shape and size. In some examples, insertion device 100 is manufactured with an adhesive liner overlying adhesive element 110, and the adhesive liner is peeled away to expose the sticky surface of adhesive element 110.

Device housing 102 may include a base surface 112 (which is covered by the adhesive element 110 in FIG. 2). Base surface 112 may be configured to serve as the user-mounting structure of insertion device 100. In examples, base surface 112 defines at least one hole forming an opening through device housing 102. For example, as depicted at FIG. 1, device housing 102 may define a first hole 114 and/or a second hole 116. Holes 114, 116 may further form an opening through adhesive element 110 when adhesive element 110 covers some portion of base surface 112.

First hole 114 and/or second hole 116 may be defined to accommodate passage of an insertion needle and a medical device from a position within device housing 102 to a position at least partially outside of device housing 102. In examples, first hole 114 is configured (e.g., shaped, sized, and/or located) to accommodate passage of a first insertion needle and a first medical device (e.g., a fluid delivery cannula) from a position within device housing 102 to a position at least partially outside of device housing 102, and second hole 116 is configured (e.g., shaped, sized, and/or located) to accommodate passage of a second insertion needle and a second medical device (e.g., an analyte sensor) from another position within device housing 102 to another position at least partially outside of device housing 102. First hole 114 and/or second hole 116 may be configured to accommodate retraction of the first insertion needle and the second insertion needle respectively from a position outside device housing 102 to a position within device housing 102. In examples, first hole 114 and second hole 116 are located to allow sufficient spacing in or under the skin of the user to avoid interference between a fluid delivered through a fluid delivery cannula and an operation of an analyte sensor. For example, first hole 114 and second hole 116 may be defined at substantially opposite ends of base surface 112.

FIG. 3 depicts insertion device 100 in schematic form. Insertion device 100 is depicted proximate to (e.g., in contact with) the skin 118 of a user. A first medical device 120 is implanted in the user and extends through first hole 114 from a position within device housing 102 to a position outside of device housing 102 (e.g., a first location under the skin 118). A second medical device 122 is implanted in the user and extends through second hole 116 from another position within device housing 102 to another position outside of device housing 102 (e.g., a second location under the skin 118). In examples, first medical device 120 is a fluid delivery cannula configured to deliver a fluid (e.g., insulin) to the first location and second medical device 122 is an analyte sensor and/or communication links engaged with the analyte sensor configured to sense a physiological charac- teristic (e.g., a glucose level) at the second location. Inser- tion device 100 is configured to implant first medical device 120 and second medical device 122 such that the first location and the second location are separated by a displace- ment D. In examples, insertion device 100 is configured to cause the implantation of first medical device 120 in a first direction S1 (e.g., using first insertion needle 132 (FIGS. 4, 5A-5C, 6A-6C)) and cause implantation of second medical device 122 in a second direction S2 (e.g., using second insertion needle 134 (FIGS. 4, 5A-5C, 6A-6C)) different from the first direction S1. FIG. 3 further depicts adhesive element 110 configured to substantially secure the device housing 102 to the skin of the user.

As will be discussed, an insertion mechanism unit 124 may be configured to cause implantation of first medical device 120 and second medical device 122 within the user when, for example, the user actuates insertion mechanism unit 124 using user input device 108. Insertion mechanism unit 124 may be configured to cause a first insertion needle (e.g., first insertion needle 132 (FIGS. 4, 5A-5C, 6A-6C)) to extend through first hole 114 to implant first medical device 120 (e.g., a fluid delivery cannula), and configured to cause the first insertion needle to retract back through first hole 114 while first medical device 120 remains implanted. Insertion mechanism unit 124 may be configured to cause a second insertion needle (e.g., second insertion needle 134 (FIG. 4, 5A, 5B)) to extend through second hole 116 to implant second medical device 122 (e.g., an analyte sensor), and configured to cause the second insertion needle to retract back through second hole 116 while second medical device 122 remains implanted. Insertion mechanism unit 124 may include a housing 126 ("mechanism housing 126") config- ured to mechanically support components of insertion mechanism unit 124. Mechanism housing 126 may be configured to couple with housing 102, and may be config- ured to detach from device housing 102 as device housing 102 remains proximate to the skin 118 of the user. A fluid infusion system 128 may be configured to deliver a fluid (e.g., insulin) to the user. A sensor system 130 may be configured to monitor an physiological characteristic of the user (e.g., a glucose level).

Figure 4:
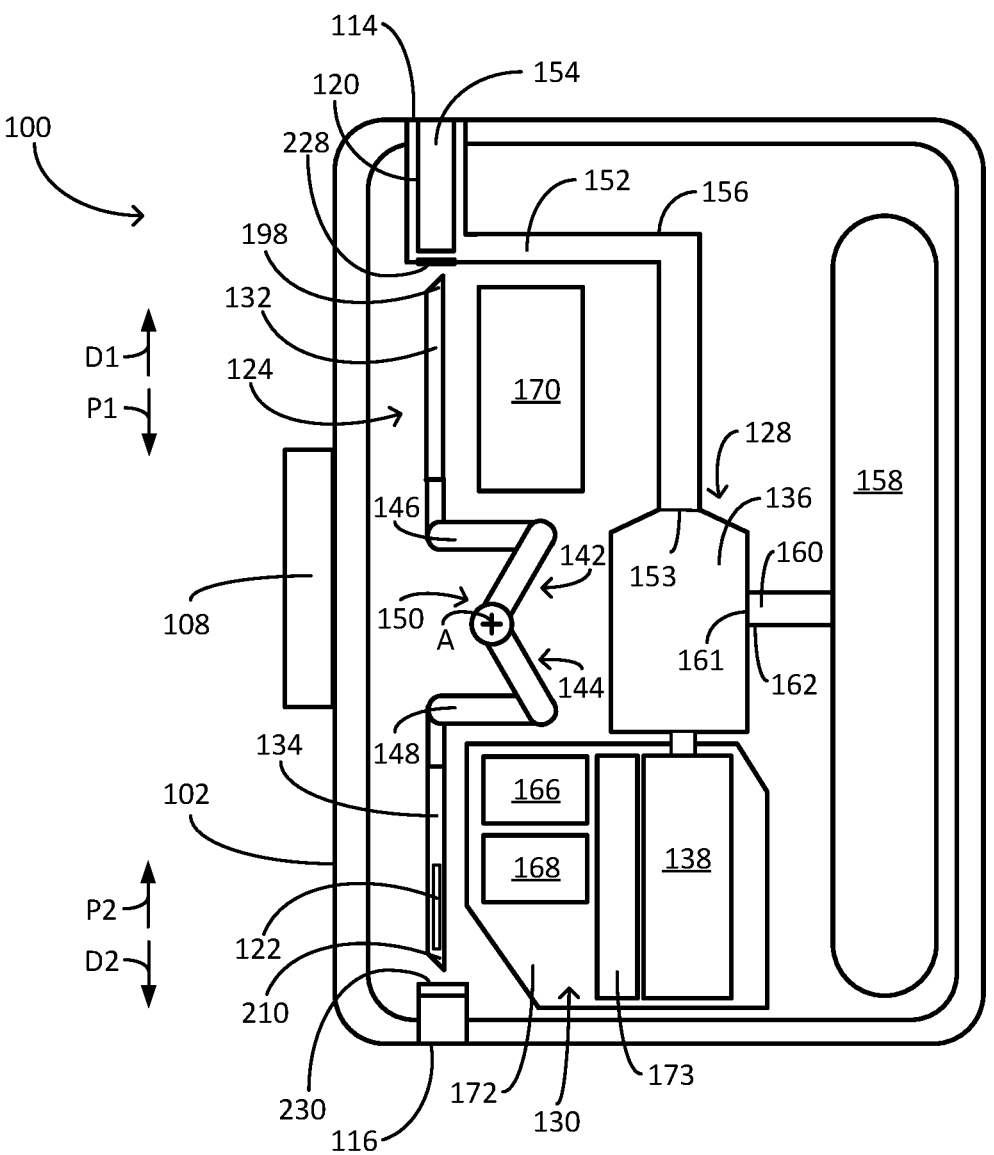
FIG. 4 is a simplified block diagram representation of a medical system.

FIG. 4 is an example simplified block diagram represen- tation of insertion device 100 including device housing 102, user input device 108, first medical device 120, second medical device 122, insertion mechanism unit 124 including a first insertion needle 132 and a second insertion needle 134, fluid infusion system 128 including a fluid pump 136 and a pump motor 138, and sensor system 130. First insertion needle 132 is configured to releasably engage first medical device 120. Second insertion needle 134 is releas- ably engaged with second medical device 122. Insertion device 100 is configured to cause first insertion needle 132 to move in the first distal direction D1 to cause implantation of first medical device 120 in the user. Insertion device 100 is configured to cause second insertion needle 134 to move in the second distal direction D2 to cause implantation of second medical device 122 in the user. Insertion device 100 is configured to retract first insertion needle 132 and second insertion needle 134 in the first proximal direction P1 and the second proximal direction P2 respectively while first medical device 120 and second medical device 122 remain implanted in the user.

Insertion device 100 may be configured to provide a fluid (e.g., insulin) to a user using, for example, first medical device 120. Insertion device 100 may be configured to provide the fluid when first medical device 120 is implanted within the user (FIG. 3). Insertion device 100 may be configured to monitor a physiological characteristic (e.g., a glucose level) of the user using, for example, second medi- cal device 122. Insertion device 100 may be configured to monitor the physiological characteristic when second medi- cal device 122 is implanted within the user (FIG. 3). Insertion mechanism unit 124 is configured to cause first insertion needle 132 and second insertion needle 134 to extend away from device housing 102 and/or mechanism housing 126 ("housing 102, 126") to implant first medical device 120 and second medical device 122 respectively into the user, and configured to cause first insertion needle 132 and second insertion needle 134 to retract toward housing 102, 126 as first medical device 120 and second medical device 122 remain implanted. In examples, first insertion needle 132 is configured to implant first medical device 120 via first hole 114 and second insertion needle 134 is con- figured to implant second medical device 122 via second hole 116.

Insertion mechanism unit 124 includes a first linkage assembly 142 and a second linkage assembly 144. First linkage assembly 142 is configured to cause first insertion needle 132 to extend away from housing 102, 126 and retract towards housing 102, 126 when some portion of first linkage assembly 142 rotates with respect to housing 102, 126. Second linkage assembly 144 is configured to cause second insertion needle 134 to extend away from housing 102, 126 and retract towards housing 102, 126 when some portion of second linkage assembly 144 rotates with respect to housing 102, 126. First linkage assembly 142 may include an input link 146 ("first input link 146") configured to rotate relative to housing 102, 126. Second linkage assembly 144 may include an input link 148 ("second input link 148") configured to rotate relative to housing 102, 126. In examples, housing 102, 126 defines a central axis A, and first linkage assembly 142 (e.g., an end of first input link 146) and/or second linkage assembly 144 (e.g., an end of second input link 148) is configured to rotate substantially around central axis A. In FIG. 4, central axis A is shown perpen- dicular to the page.

Insertion mechanism unit 124 further includes a driver 150 configured to cause the rotation of first assembly 142 and second assembly 144. Driver 150 may be configured to cause the rotation of first assembly 142 and the rotation second linkage assembly 144 substantially concurrently. In examples, user input device 108 is configured to cause driver 150 to rotate first linkage assembly 142 and second linkage assembly 144, such that the user may control the implanta- tion of first medical device 120 and second medical device 122. In some examples, as will be discussed, driver 150 may include a spring configured to cause first assembly 142 and/or second assembly 144 to rotate relative to housing 102, 126. In some examples, the spring is a torsion spring configured to release from a wound position to an unwound position to cause the rotations of first assembly 142 and/or second assembly 144.

Insertion device 100 may be configured to define a first flow path 152 from a discharge of fluid pump 136 to first medical device 120. In examples, first medical device 120 is a fluid delivery cannula defining an interior lumen 154, and insertion device 100 is configured to provide a first flow path 152 from a discharge 153 of fluid pump 136 through lumen 154 of the fluid delivery cannula. In examples, insertion device 100 includes a first conduit 156 configured to define first flow path 152. Insertion device 100 may further define a fluid reservoir 158 (e.g., with device housing 102 and/or fluid cartridge 104 (FIGS. 1, 2)) and be configured to define a second flow path 160 from reservoir 158 to a suction 161 of fluid pump 136. In examples, insertion device 100 includes a second conduit 162 configured to define second flow path 160. The fluid pump 136 may include a motor 138 configured to cause fluid pump 136 to create pressure to deliver fluid (e.g., via first flow path 152). Fluid infusion system 128 may include one or more of fluid pump 136, motor 138, first conduit 156, fluid reservoir 163, and/or second conduit 162.

Insertion device 100 may include one or more of a processor device 166; a memory element 168 to store data, processor-readable program instructions, and the like; a battery 170 or other power source; and a sensor interface 173 configured to establish electrical connectivity with a medical device, such as second medical device 122. Processor device 166, memory element 168, battery 170, and/or sensor interface 173 may be included on an electronics assembly 172. In examples, second medical device 122 is an analyte sensor configured to electrically couple to sensor interface 173 to establish electrical connectivity between conductors of the analyte sensor and conductors of the electronics assembly 172. Electronics assembly 172 (or the components of electronics assembly 172) can be electrically coupled to other elements of insertion device 100 as needed to support the operation of insertion device 100. For example, the electronics assembly 172 can be electrically coupled to at least the following, without limitation: the fluid pump 136; the sensor interface 173; the insertion mechanism unit 124; and the user input device 108. It should be appreciated that electrical connections to the electronics assembly 172 can be direct or indirect if so desired. Moreover, one or more components of the electronics assembly 172 may support wireless data communication in some embodiments.

In examples, processor device 166 includes processing circuitry configured to control an operation of fluid pump 136. For example, the processing circuitry may be configured to cause the fluid pump 136 to commence, continue, and/or cease transporting fluid from fluid reservoir 158 to first medical device 120 (e.g., a fluid delivery cannula). In examples, at least one of first medical device 120 or second medical device 122 is an analyte sensor configured to generate a signal indicative of a physiological characteristic of the user (e.g., a glucose level), and the processing circuitry is configured to determine the physiological characteristic using the indicative signal. In some examples, the processing circuitry is configured to control an operation of fluid pump 136 based on the indicative signal reported by the analyte sensor. Sensor system 130 may include one or more of sensor interface 173, first medical device 120, and/or second medical device 122.

Device housing 102 is suitably shaped, sized, and configured to house or support the electronics assembly 172, the fluid pump 136, the fluid reservoir 158, the sensor interface

173, and the user interface device 108. The fluid infusion system 128 depicted in FIG. 3 may include at least the fluid pump 136, the fluid reservoir 158, first conduit 156, and second conduit 162 shown in FIG. 4. The sensor system 130 depicted in FIG. 3 may include at least the sensor interface 173 shown in FIG. 4.

As discussed, insertion device 100 may be configured to cause first insertion needle 132 and second insertion needle 134 to implant first medical device 120 and second medical device 122 substantially concurrently. Insertion device 100 may be configured to cause first insertion needle 132 extend in a first direction away from housing 102, 126 and cause second insertion needle 134 to extend in a different, second direction away from housing 102, 126, in order to implant first medical device 120 at a location displaced from second medical device 122. Insertion device 100 includes an insertion mechanism unit 124 which may be activated by the user and configured to cause the implantation of first medical device 120 and second medical device 122.

Figure 5C:
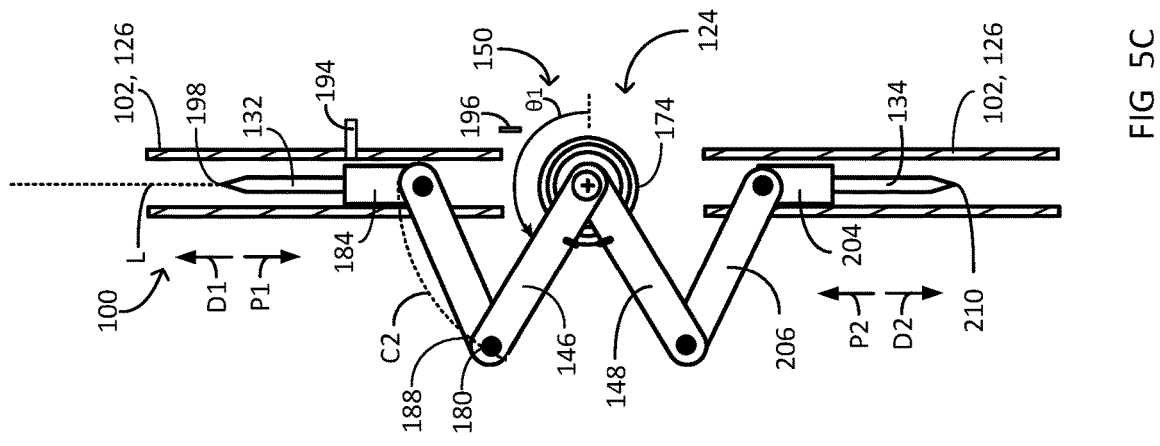
FIG. 5C is a schematic of the insertion device of FIG. 5A and FIG. 5B in a stowed configuration.
Figure 5B:
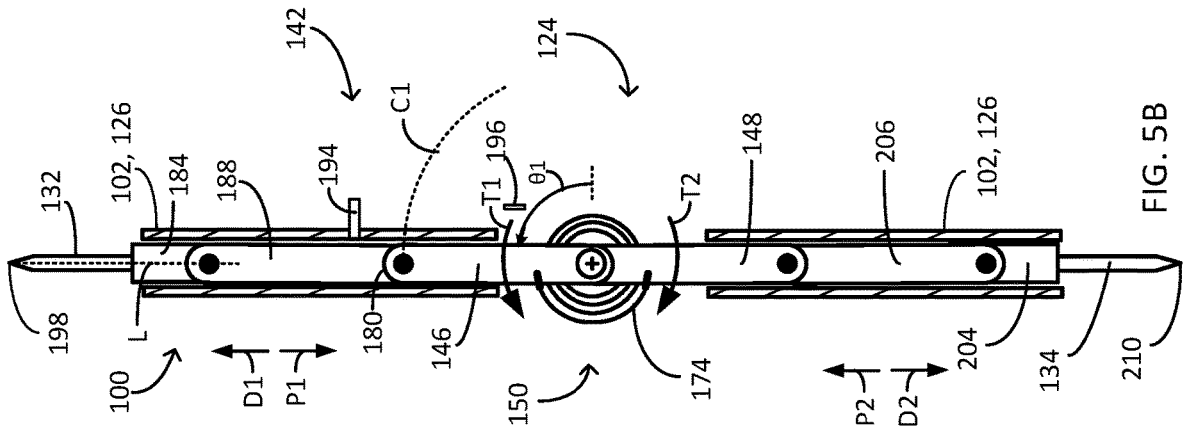
FIG. 5B is a schematic of the insertion device of FIG. 5A in a deployed configuration.
Figure 5A:
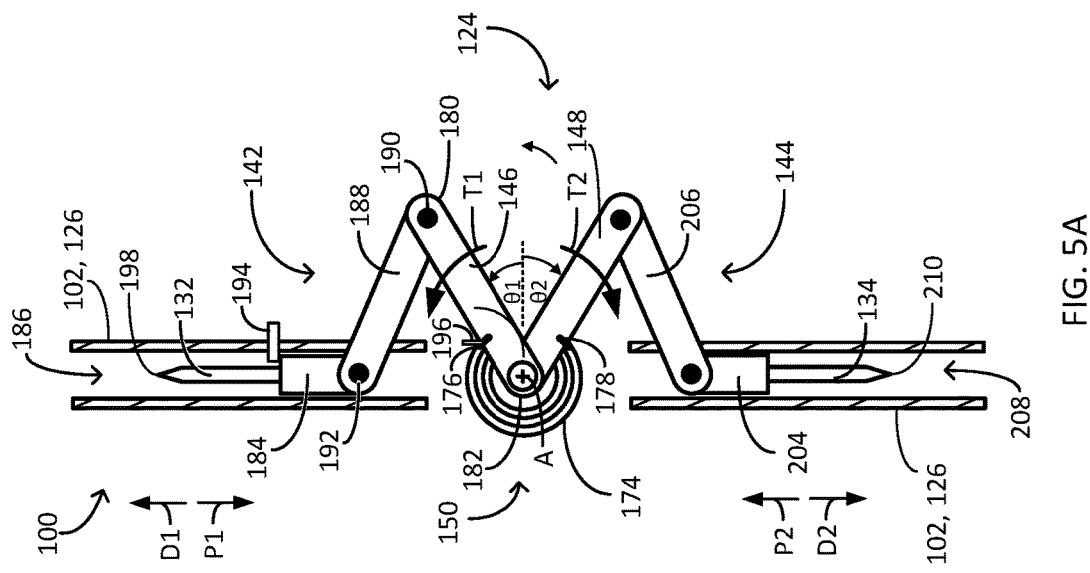
FIG. 5A is a schematic of an example insertion device in an undeployed configuration.

FIG. 5A, FIG. 5B, and FIG. 5C. Schematically illustrate an insertion mechanism unit 124 including driver 150. Insertion mechanism unit 124 includes first linkage assembly 142 configured to cause first insertion needle 132 to extend and retract relative to housing 102, 126. Insertion mechanism unit 124 includes second linkage assembly 144 configured to cause second insertion needle 134 to extend and retract relative to housing 102, 126. Central axis A is included for reference. Driver 150 is configured to drive first linkage assembly 142 and second linkage assembly 144 from the configuration of FIG. 5A to the configuration of FIG. 5B to extend first insertion needle 132 and second insertion needle 134 in a direction away from housing 102, 126, and to drive first linkage assembly 142 and second linkage assembly 144 from the configuration of FIG. 5B to the configuration of FIG. 5C to retract first insertion needle 132 and second insertion needle 134 in a direction toward housing 102, 126.

In examples, driver 150 includes a spring 174 configured to drive first linkage assembly 142 and second linkage assembly 144. Insertion device 100 may be configured such that spring 174 is in a wound and/or charged condition when the user positions insertion device 100 proximate to the skin. For example, insertion device 100 may be manufactured and/or assembled such that spring 174 is in a wound and/or charged condition when delivered to the user. The user may actuate user input device 108 to cause operation of a release mechanism unit configured to allow spring 174 to unwind and/or discharge to cause movement of first linkage assembly 142, and/or second linkage assembly 144. For example, the release mechanism unit may be a mechanical stop having a first position where the mechanical stop engages spring 174, first linkage assembly 142, and/or second linkage assembly 144 to substantially prevent motion of spring 174, first linkage assembly 142, and/or second linkage assembly 144, such that spring 174 is prevented from unwinding and/or discharging. The mechanical stop may have a second position where the mechanical stop is substantially disengaged from spring 174, first linkage assembly 142, and/or second linkage assembly 144, such that spring 174 is substantially free to unwind and/or discharge to cause motion of first linkage assembly 142 and/or second linkage assembly 144. Insertion device 100 may be configured such that a user may cause the release mechanism unit to shift from the first position to the second position using user input device 108.

In examples, driver 150 includes a spring 174 configured to cause a rotation of first linkage assembly 142 (e.g., first input link 146) and/or second linkage assembly 144 (e.g., second input link 148) relative to housing 102, 126. Spring 174 may be configured to convert potential energy into kinetic energy to cause the rotation. For example, spring 174 may be in a charged condition having a first potential energy when insertion mechanism unit 124 is in the configuration of FIG. 5A. Spring 174 may convert some portion of the first potential energy to kinetic energy to transition insertion mechanism unit 124 from the configuration of FIG. 5A to the configuration of FIG. 5B, such that spring 174 is in a partially uncharged state having a second potential energy less than the first potential energy. Spring 174 may convert some portion of the second potential energy to kinetic energy to transition insertion mechanism unit 124 from the configuration of FIG. 5B to the configuration of FIG. 5C, such that spring 174 is in a substantially relaxed state having a third potential energy less than the second potential energy.

In examples, spring 174 is a torsion spring having a first end 176 ("spring first end 176") and a second end 178 ("spring second end 178"). The torsion spring may be configured to store potential energy by substantially winding (e.g., twisting around) a spring axis, and may be configured to cause movement of spring first end 176 and spring second end 178 as the torsion spring unwinds to expend the potential energy. In examples, the spring axis may be substantially parallel to and/or coincident with central axis A. Spring first end 176 may be configured to exert a first torque T1 (e.g., around central axis A) on first linkage assembly 142 when spring 174 expends potential energy, and may be configured to exert a second torque T2 (e.g., around central axis A) on second linkage assembly 144 when spring 174 expends potential energy. In examples, first torque T1 and second torque T2 have opposite rotational directions.

First input link 146 of first linkage assembly 142 is configured to rotate relative to housing 102, 126 when the first torque T1 is exerted on first input link 146 by driver 150. In examples, first input link 146 is configured such that a terminal end 180 of first input link 146 rotates substantially around central axis A when the first torque T1 is exerted on first input link 146. In some examples, first input link 146 is rotatably pinned to housing 102, 126 or another portion of insertion device 100 at a first end 182 opposite terminal end 180, such that terminal end 180 is constrained to define a circular path substantially around first end 182 when the first torque T1 is exerted on first input link 146.

First linkage assembly 142 includes a plurality of links including first input link 146 and a first output link 184. First input link 146 and first output link 184 define a first kinematic chain, such that a rotation of first input link 146 relative to housing 102, 126 causes motion of first output link 184 relative to first input link 146, and relative to housing 102, 126. For example, first input link 146 may define an input angle θ1 (e.g., a crank angle) relative to a portion of housing 102, 126. First linkage assembly may define the first kinematic chain such that, as the input angle θ1 increases or decreases during rotation of first input link 146, the first kinematic chain causes first output link 184 to move relative to first input link 146 and housing 102, 126.

In examples, first output link 184 is a sliding member configured to linearly translate relative to housing 102, 126 when first input link 146 rotates relative to housing 102, 126. First output link 184 may be configured to linearly translate within a first channel 186 defined by housing 102, 126. For example, first linkage assembly 142 may be configured such that first output link 184 slidably translates within first channel 186 in the distal direction D1 when first input link 146 initially increases the input angle θ1 (e.g., up to about 90 degrees (FIG. 5B)), and may be configured such that first output link 184 slidably translates within first channel 186 in the proximal distal direction P1 as first input link 146 further increases the input angle θ1 (e.g., beyond about 90 degrees (FIG. 5C)). First output link 184 is mechanically engaged with first insertion needle 132, such that translation of first output link 184 in the distal direction D1 causes first insertion needle 132 to extend in a direction away from housing 102, 126, and translation of first output link 184 in the proximal direction P1 causes first insertion needle 132 to retract in a direction toward housing 102, 126.

In examples, first linkage assembly 142 includes a medial link 188 ("first medial link 188") rotatably engaged with terminal end 180 and first output link 184. In examples, first medial link 188 is configured as a floating link in the first kinematic chain defined by first linkage assembly 142. For example, first medial link 188 may be rotatably engaged with terminal end 180 by a joint 190 configured to allow relative rotation of first medial link 188 and first input link 146. First medial link 188 may be rotatably engaged with first output link 184 by a joint 192 configured to allow relative rotation between first medial link 188 and first output link 184. First linkage assembly 142 may include any number of floating links in the first kinematic chain defined by first input link 146 and first output link 184.

FIG. 5B illustrates first linkage assembly 142 with driver 150 (e.g., spring 174) having expended potential energy to exert the torque T1 on first input link 146. The torque T1 has caused first input link 146 to rotate relative to housing 102, 126, such that first input link 146 defines the input angle θ1 at about 90 degrees. The rotation of first input link 146 relative to housing 102, 126 has caused terminal end 180 to travel over the substantially circular path C1 around first end 182 compared to FIG. 5A, causing first linkage assembly 142 (e.g., first medial link 188) to drive first output link 184 and first insertion needle 132 over the substantially linear path L in a direction away from housing 102, 126 (e.g., in the distal direction D1). Torsion spring 174 may continue to exert the torque T1 on first input link 146 to further increase the input angle θ1 as spring 174 continues to unwind.

FIG. 5C illustrates first linkage assembly 142 with torsion spring 174 having expended additional potential energy to rotate first input link 146 such that first input link 146 defines the input angle θ1 at greater than 90 degrees. The rotation of first input link 146 relative to housing 102, 126 has caused terminal end 180 to travel over the substantially circular path C2 around first end 182 compared to FIG. 5B, causing first linkage assembly 142 (e.g., first medial link 188) to drive first output link 184 and first insertion needle 132 over the substantially linear path L in a direction toward housing 102, 126 (e.g., in the proximal direction P1). In examples, driver 150 (e.g., spring 174) has expended substantially all of its potential energy and is in a relaxed state when first insertion needle 132 has been retracted into housing 102, 126, such that driver 150 no longer exerts the first torque T1 on first linkage assembly 142, although this is not required.

Insertion device 100 is configured to substantially maintain spring 174 in the charged state to prevent spring 174 from causing rotation of first linkage assembly 142 and/or second linkage assembly 144 until user input device 108 (FIG. 1, 4) is actuated. For example, insertion mechanism unit 124 may include a release mechanism unit (e.g., mechanical stops 194, 196 discussed below) configured to engage spring 174, first linkage assembly 142, second linkage assembly 144, and/or some other portion of insertion mechanism unit 124 to substantially constrain movement of insertion mechanism unit 124, such that spring 174 is substantially prevented from expending potential energy to cause movement of insertion mechanism unit 124. User input device 108 may be configured to cause the release mechanism unit to disengage from insertion mechanism unit 124, such that insertion mechanism unit 124 is substantially free to move and spring 174 may expend potential energy to drive the movement. In some examples, the release mechanism unit is configured to engage first linkage assembly 142 such that first linkage assembly 142 is constrained from movement caused by the first input torque T1 exerted by driver 150. In some examples, the release mechanism unit is configured to mechanically engage driver 150 (e.g., spring 174) to substantially prevent driver 150 from exerting the first torque T1 on first linkage assembly 142.

For example, insertion device 100 may include a mechanical stop 194 configured to constrain movement of first linkage assembly 142 in a first position. Mechanical stop 194 is depicted in FIG. 5A as mechanically engaging first output link 184, however mechanical stop 194 may have any orientation and engage any portion of first linkage assembly 142 in the first position. Mechanical stop 194 is configured to engage first linkage assembly 142 such that first linkage assembly 142 is constrained from movement caused by the first input torque T1 exerted by driver 150. Mechanical stop 194 may be configured to mechanically disengage from first linkage assembly 142 such that first torque T1 causes a rotation of first linkage assembly 142 (e.g., first input link 146). In examples, mechanical stop 194 is configured to establish the first position (e.g., FIG. 5A) wherein mechanical stop 194 mechanically engages first linkage assembly 142 and establish a second position (e.g., FIG. 5B and/or FIG. 5C) wherein mechanical stop 194 is mechanically disengaged from first linkage assembly 142. User input device 108 may be configured to cause mechanical stop 194 to transition from the first position to the second position. User input device 108 may be coupled with the mechanical stop 194 wirelessly, electrically, mechanically or in any other effective way.

In some examples, instead of or in addition to mechanical stop 194, insertion device 100 may include a mechanical stop 196 configured to constrain movement spring 174 from exerting the first torque T1 on first linkage assembly 142 in a first position. Mechanical stop 196 is depicted in FIG. 5A as mechanically engaging first spring end 176, however mechanical stop 196 may have any orientation and engage any portion of driver 150 in the first position. Mechanical stop 196 is configured to engage driver 150 such that spring 174 is substantially prevented from exerting the first torque T1 on first linkage assembly 142. Mechanical stop 196 may be configured to mechanically disengage from driver 150 such that spring 174 exerts the first torque T1 on first linkage assembly 142 (e.g., on first input link 146). In examples, mechanical stop 196 is configured to establish the first position (e.g., FIG. 5A) wherein mechanical stop 196 mechanically engages driver 150 and establish a second position (e.g., FIG. 5B and/or FIG. 5C) wherein mechanical stop 196 is mechanically disengaged from driver 150. User input device 108 may be configured to cause mechanical stop 196 to transition from the first position to the second position. User input device 108 may be coupled with the mechanical stop 196 wirelessly, electrically, mechanically or in any other effective way.

Mechanical stops 194, 196 are examples of a release mechanism unit. Insertion device 100 may include any release mechanism unit configured to substantially maintain spring 174 in the charged state to prevent spring 174 from causing rotation of first linkage assembly 142 and/or second linkage assembly 144 until user input device 108 (FIG. 1, 4) is actuated.

Driver 150 may use any elastic object configured to store mechanical energy as potential energy and configured to cause the rotation of first linkage assembly 142 and/or second linkage assembly 144 using an expenditure of the potential energy. Spring 174 may be any type of spring. For example, spring 174 may be torsion spring discussed above, a compression spring, a leaf spring, a spiral spring, a flat spring, a machined spring, a serpentine spring, a garter spring, or another type of spring configured to store potential energy. Spring 174 may be a constant force or variable force spring. Driver 150 may use any number of springs and any type of spring in any combination to cause the rotation of first linkage assembly 142 and second linkage assembly 144.

Driver 150 including spring 174 is one example of a driver configured to cause rotation of first linkage assembly 142 and/or second linkage assembly 144. Driver 150 may cause the rotation of first linkage assembly 142 and/or second linkage assembly 144 in any manner. In examples, driver 150 includes one or more motors configured to cause the rotation of first linkage assembly 142 and/or second linkage assembly 144. The one or more motors may be, for example, a rotary motor configured to cause the rotation using a rotation of an output shaft, a linear motor configured to cause the rotation using translation of a slider, or other type of motors configured to produce an output motion (e.g., relative to a motor housing) and use the output motion to cause the rotation. The one or more motors may be constant or variable speed motors, and may be configured to cause the rotation of first linkage assembly 142 and/or second linkage assembly 144 at a constant rotational speed or a varying rotational speed. In examples, the one or more motors are be configured to receive power from a battery (e.g., battery 170) within insertion device 100. Insertion device 100 may include processing circuitry configured to control the one or motors (e.g., configured to cause a motor to generate motion, to cease generating motion, to generate motion at a particular speed, etc.) In examples, user input device 108 is configured to actuate the one or more motors to cause the rotation of first linkage assembly 142 and/or second linkage assembly 144.

Hence, first linkage assembly 142 is configured to cause first insertion needle 132 to extend in a first direction away from housing 102, 126 (e.g., the distal direction D1) and subsequently withdraw in a direction toward housing 102, 126 (e.g., the proximal direction P1) when first linkage assembly 142 (e.g., first input link 146) rotates relative to housing 102, 126. In examples, first insertion needle 132 defines a distal end 198 ("first needle distal end"), and first linkage assembly 142 is configured to cause first insertion needle 132 to transition from a first undeployed position wherein first needle distal end 198 is within housing 102, 126 (e.g., within first channel 186 (FIG. 5A)) to a first deployed position wherein first needle distal end 198 is outside housing 102, 126 (e.g., outside of first channel 186 (FIG. 5B)). In examples, first linkage assembly 142 is configured to cause first insertion needle 132 to transition from the first deployed position (FIG. 5B) to a first stowage position wherein first needle distal end 198 is within housing 102, 126 (e.g., inside of first channel 186 (FIG. 5C)). The first stowage position may be a different position that the first undeployed position, or may be substantially the same position as the first undeployed position.

Insertion mechanism unit 124 further includes second linkage assembly 144, including second input link 148, second output link 204, and second medial link 206, which may be configured similarly to and in relation to each other in the same manner as that described for first input link 146, first output link 184, and first medial link 188 respectively. For example, second linkage assembly 144 may be configured such that the torque T2 exerted on second input link 148 by driver 150 (e.g., via spring second end 178) causes second output link 204 to translate within a second channel 208 defined by housing 102, 126 in a distal direction D2 and subsequently in a proximal direction P2. Second output link 204 may be mechanically engaged with second insertion needle 134, such that translation of second output link 204 causes second insertion needle 134 to extend in a direction away from housing 102, 126 and to retract in a direction toward housing 102, 126. Second input link 148 may define an input angle θ2 (e.g., a crank angle) relative to a portion of housing 102, 126.

In examples, second insertion needle 134 defines a distal end 210 ("second needle distal end"), and second linkage assembly 144 is configured to cause second insertion needle 134 to transition from a second undeployed position wherein second needle distal end 210 is within housing 102, 126 (e.g., within second channel 208 (FIG. 5A)) to a second deployed position wherein second needle distal end 210 is outside housing 102, 126 (e.g., outside of second channel 208 (FIG. 5B)). In examples, second linkage assembly 144 is configured to cause second insertion needle 134 to transition from the second deployed position (FIG. 5B) to a second stowage position wherein second needle distal end 210 is within housing 102, 126 (e.g., inside of second channel 208 (FIG. 5C)). The second stowage position may be a different position that the second undeployed position, or may be substantially the same position as the second undeployed position.

Insertion device 100 may include a mechanical stop (not shown) configured relative to second linkage assembly 144 and user input device 108 in the same or similar manner as mechanical stop 194 is configured relative to first linkage assembly 142 and user input device 108. Insertion device 100 may include a mechanical stop (not shown) configured relative to driver 150 (e.g., second spring end 178) and user input device 108 in the same or similar manner as mechanical stop 196 is configured relative to driver 150 (e.g., first spring end 176) and user input device 108.

The rotation of first input link 146 and/or second input link 148 may be in one, continuous, direction. The continuous direction may be clockwise or counter-clockwise. Further, input angle θ1 and/or input angle θ2 may be any angle. In an example, insertion device 100 is configured to cause first input link 146 and/or second input link 148 to define input angle θ1 and/or input angle θ2 within some range between 0 degrees to 180 degrees (e.g., within a range from about 30 degrees to about 150 degrees, from about 45 degrees to about 135 degrees, or some other range defined between 0 degrees to 180 degrees). Additionally rotation of first input link 146 and second input link 148 may be substantially synchronized such that first input angle θ1 and second input angle θ2 describe substantially equal angles as driver 150 causes rotation of first input link 146 and second input link 148, however this is not required. In some examples, first input link 146 and second input link 148 may be non-synchronized, such that first input angle θ1 and second input angle θ2 describe substantially unequal input angles as driver 150 causes rotation of first input link 146 and second input link 148. In a non-synchronized implementation, the first input angle θ1 and second input angle θ2 during movement may differ, with respect to the same time, from one another. Additionally, the lengths of first input link 146, first medial link 188, first output link 184, second input link 148, second medial link 206, second output link 204, and/or other links within first linkage assembly 142 or second linkage assembly 144 may be varied to adjust rotational symmetry, timing, the insertion depths of first insertion needle 132 and/or second insertion needle 134, or for other reasons.

Figure 6C:
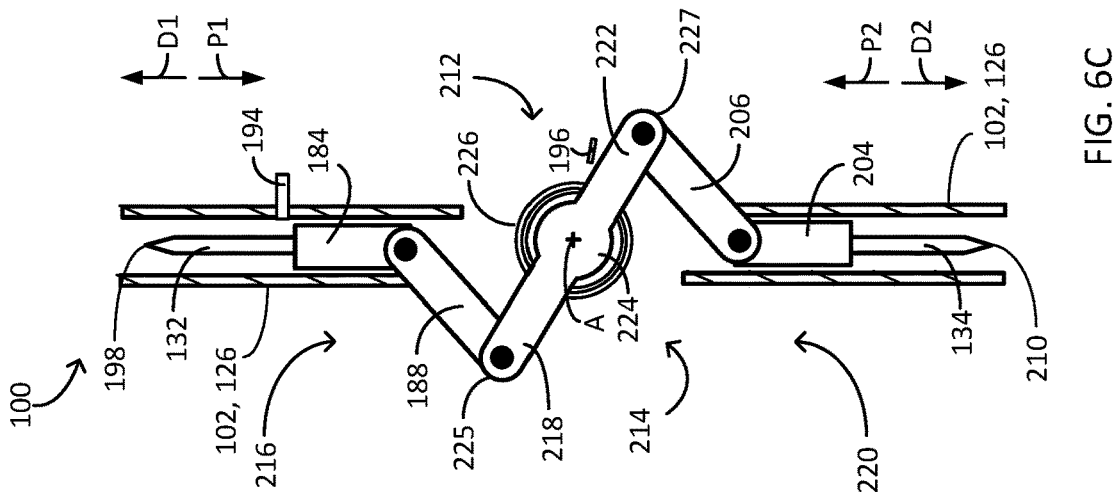
FIG. 6C is a schematic of the insertion device of FIG. 6A and FIG. 6B in a stowed configuration.
Figure 6B:
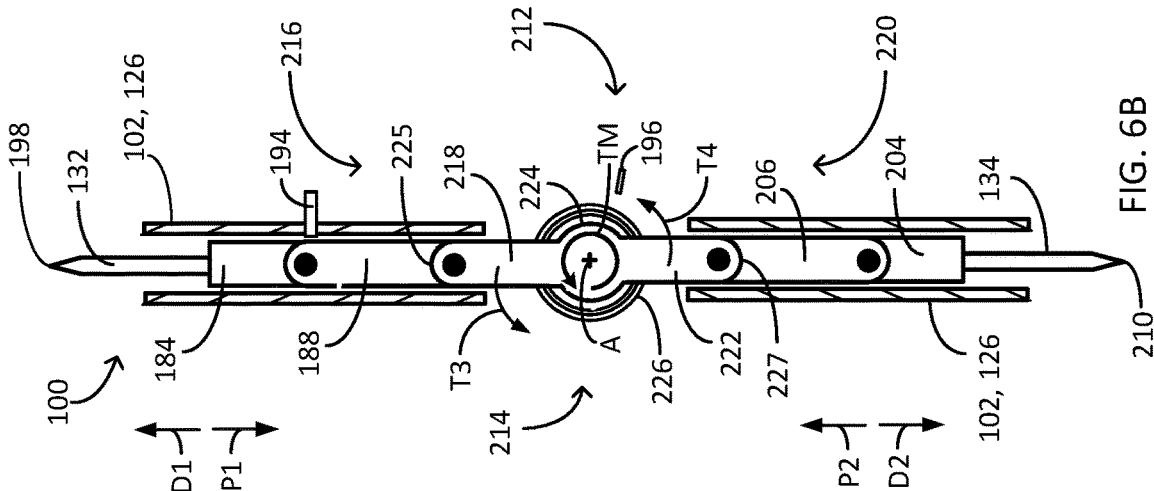
FIG. 6B is a schematic of the insertion device of FIG. 6A in a deployed configuration.
Figure 6A:
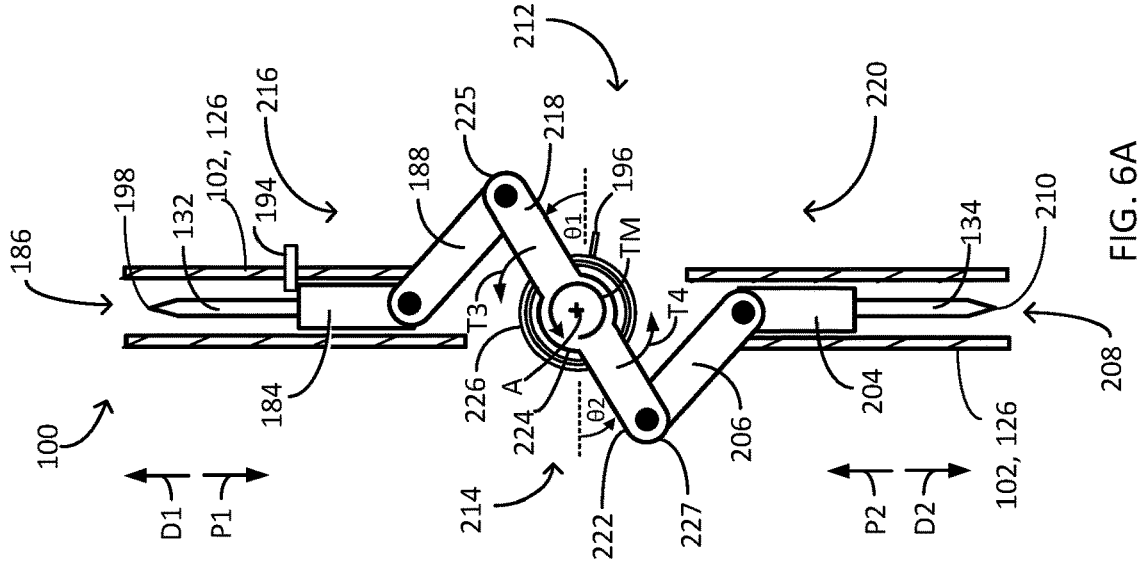
FIG. 6A is a schematic of an example insertion device in an undeployed configuration.

FIG. 6A, FIG. 6B, and FIG. 6C schematically illustrate another example insertion mechanism unit 212 including driver 214. Insertion mechanism unit 212 includes first linkage assembly 216 including first input link 218 and second linkage assembly 220 including second input link 222. Driver 214 is configured to exert a torque T3 on first linkage assembly 216 (e.g., first input link 218) and a torque T4 on second linkage assembly 220 (e.g., second input link 222) to cause first insertion needle 132 and second insertion needle 134 to extend and retract relative to housing 102, 126. Driver 214 is configured to exert torque T3 on first linkage assembly 216 and torque T4 on second linkage assembly 220 in the same rotational direction around central axis A. Insertion mechanism unit 212, first linkage assembly 216, first input link 218, second linkage assembly 220, and second input link 222 may be examples of insertion mechanism unit 124, first linkage assembly 142, first input link 146, second linkage assembly 144, and second input link 148 respectively.

Driver 214 includes a hub 224 configured to revolve around an axis defined by housing 102, 126, such as central axis A. Hub 224 may be configured to revolve relative to housing 102, 126. Driver 214 is configured to impart a torque TM on hub 224 to cause the revolution. Hub 224 may be configured to transmit some portion of the torque TM to first input link 218, such that first input link 218 experiences the torque T3 in the same direction as the torque TM. Hub 224 may be configured to transmit some portion of the torque TM to second input link 222, such that second input link 218 experiences the torque T4 in the same direction as the torque TM. In examples, first input link 218 and second input link 222 mechanically engage hub 224 such that the revolution of hub 224 (e.g., around central axis A) driven by torque TM causes a rotation of first input link 218 and second input link 222 relative to housing 102, 126. For example, the revolution of hub 224 may cause a first terminal end 225 of first input link 218 to rotate around hub 224, and may cause a second terminal end 227 of second input link 222 to rotate around hub 224.

First input link 218 and first output link 184 define a kinematic chain, such that a rotation of first input link 218 relative to housing 102, 126 causes motion of first output link 184 relative to first input link 218 and relative to housing 102, 126. The kinematic chain defined by first input link 218 and first output link 184 may be configured in the same or a similar manner to the first kinematic chain defined by first input link 146 (FIGS. 4, 5A-5C) and first output link 184. Second input link 222 and second output link 204 define an additional kinematic chain, such that a rotation of second first input link 218 relative to housing 102, 126 causes motion of second output link 184 relative to second input link 222 and relative to housing 102, 126. The additional kinematic chain defined by second input link 222 and second output link 204 may be configured in the same or a similar manner to the second kinematic chain defined by second input link 148 (FIGS. 4, 5A-5C) and second output link 204.

Thus, first linkage assembly 216 is configured to cause first insertion needle 132 to transition from the first undeployed position (FIGS. 5A, 6A) wherein first needle distal end 210 is within housing 102, 126 to the first deployed position (FIGS. 6A, 6B) wherein first needle distal end 210 is outside housing 102, 126, and configured to cause first insertion needle 132 to transition from the first deployed position to a first stowage position (FIGS. 5C, 6C) wherein first needle distal end 210 is within housing 102, 126. Second linkage assembly 220 is configured to cause second insertion needle 134 to transition from the second undeployed position (FIGS. 5A, 6A) wherein second needle distal end 210 is within housing 102, 126 to the second deployed position (FIGS. 5B, 6B) wherein second needle distal end 210 is outside housing 102, 126, and configured to cause second insertion needle 134 to transition from the second deployed position to the second stowage position (FIGS. 5C, 6C) wherein second needle distal end 210 is within housing 102, 126.

Driver 214 may include a spring 226 configured to exert the torque TM on hub 224 to cause the revolution of hub 224 cause the revolution of hub 224 relative to housing 102, 126. Spring 226 may be an example of spring 174. Spring 226 may be configured to convert potential energy into kinetic energy to cause the revolution of hub 224. For example, spring 226 may be in a charged condition having a primary potential energy when insertion mechanism unit 212 is the configuration of FIG. 6A. Spring 226 may convert some portion of the primary potential energy to kinetic energy to transition insertion mechanism unit 212 from the configuration of FIG. 6A to the configuration of FIG. 6B, such that spring 226 is in a partially uncharged state having a secondary potential energy less than the primary potential energy. Spring 226 may convert some portion of the secondary potential energy to kinetic energy to transition insertion mechanism unit 212 from the configuration of FIG. 6B to the configuration of FIG. 6C, such that spring 226 is in a substantially relaxed state having a tertiary potential energy less than the secondary potential energy.

In examples, spring 226 is a torsion spring configured to store potential energy by substantially winding (e.g., twisting around) a spring axis. Spring 226 may be mechanically engaged with hub 224 to cause revolution of hub 224 as the spring 226 unwinds to expend the potential energy. In examples, the spring axis may be substantially parallel to and/or coincident with central axis A. Some portion of spring 240 (e.g., a portion of the spring coil or a spring end) may be configured to exert the torque TM on hub 224 when spring 226, causing hub 224 to transmit the torque T3 to first linkage assembly 216 and the torque T4 to second linkage assembly 220. In examples, torque T3 and torque T4 have the same rotational direction.

The rotation of first input link 218 and/or second input link 222 may be in one, continuous, direction. The continuous direction may be clockwise or counter-clockwise. Further, input angle $\theta1$ and/or input angle $\theta2$ may be any angle. In an example, insertion device 100 is configured to cause first input link 218 and/or second input link 222 to define input angle $\theta1$ and/or input angle $\theta2$ within some range between 0 degrees to 180 degrees (e.g., within a range from about 30 degrees to about 150 degrees, from about 45 degrees to about 135 degrees, or some other range defined between 0 degrees to 180 degrees). Additionally rotation of first input link 218 and second input link 222 may be substantially synchronized such that first input angle $\theta1$ and second input angle $\theta2$ describe substantially equal angles as driver 214 causes rotation of first input link 218 and second input link 222, however this is not required. In some examples, first input link 218 and second input link 222 may be non-synchronized, such that first input angle $\theta1$ and second input angle $\theta2$ describe substantially unequal input angles as driver 214 causes rotation of first input link 218 and second input link 222. In a non-synchronized implementation, the first input angle $\theta1$ and second input angle $\theta2$ during movement may differ, with respect to the same time, from one another. Additionally, the lengths of first input link 218, first medial link 188, first output link 184, second input link 222, second medial link 206, second output link 204, and/or other links within first linkage assembly 216 or second linkage assembly 220 may be varied to adjust rotational symmetry, timing, the insertion depths of first insertion needle 132 and/or second insertion needle 134, or for other reasons.

First linkage assembly 142, 216 may be configured and/or supported within housing 102, 126 to cause the extension and retraction of first insertion needle 132 in any direction relative to housing 102, 126. Second linkage assembly 144, 220 may be configured and/or supported within housing 102, 126 to cause the extension and retraction of second insertion needle 132 in any direction relative to housing 102, 126. Housing 102, 126 may define first channel 186 and second channel 208 to cause output link 184 and output link 204 respectively to linearly translate in any direction relative to housing 102, 126. Further, first input link 146, 218, first output link 184, medial link 188, and/or other links within first linkage assembly 142, 216 may have any orientation relative to housing 102, 126 and each other sufficient to cause first output link 184 to translate for the extension and retraction of first insertion needle 132. First input link 146, 218, first output link 184, medial link 188, and/or other links within first linkage assembly 142, 216 may form a joint angle with an adjacent link in any orientation relative to housing 102, 126. Second input link 148, 222 second output link 204, medial link 206, and/or other links within second linkage assembly 144, 220 may have any orientation relative to housing 102, 126 and each other sufficient to cause second output link 204 to translate for the extension and retraction of second insertion needle 134. Second input link 148, 222, second output link 204, medial link 206, and/or other links within second linkage assembly 144, 220 may form a joint angle with an adjacent link in any orientation relative to housing 102, 126.

Insertion device 100 may be configured to cause the extension and retraction of first insertion needle 132 and second insertion needle 134, and the implantation of first medical device 120 and second medical device 122, at any angle relative to housing 102, 126 and/or relative to each other. Insertion device 100 may be configured to cause the extension and retraction of first insertion needle 132 and second insertion needle 134, and the implantation of first medical device 120 and second medical device 122 at any angle relative to the user when insertion device 100 is proximate the skin 118 of the user. In examples, and as depicted at FIG. 3, insertion device 100 is configured to extend first insertion needle 132 and first medical device 120 toward the user and in a first direction (e.g., the first direction S1), and extend second insertion needle 134 and second medical device 122 toward the user in a second direction (e.g., the second direction S2) different than the first direction. Insertion device 100 may be configured to cause the retraction of first insertion needle 132 in a direction substantially opposite the first direction and the retraction of second insertion needle 134 in a direction substantially opposite the second direction.

As discussed, first insertion needle 132 is configured to releasably engage first medical device 120 to cause the implantation of first medical device 120 within the user. In examples, first medical device 120 is a fluid delivery cannula configured to deliver a fluid (e.g., insulin) to a user. First insertion needle 132 and the fluid delivery cannula may be cooperatively configured and arranged such that the first insertion needle 132 releasably carries at least the a portion (e.g., a distal portion) of the fluid delivery cannula as first insertion needle 132 is caused to extend away from housing 105, 155. In some examples, first insertion needle 132 is configured to extend into lumen 154 of the fluid delivery cannula when first insertion needle 132 extends away from housing 102, 126. First insertion needle 132 and/or the fluid delivery cannula may be configured such that first insertion needle 132 mechanically engages the fluid delivery cannula when first insertion needle 132 extends in the first distal direction D1 and disengages from the fluid delivery cannula when first insertion needle retracts in the first proximal direction P1 (FIGS. 4, 5A-5C, 6A-6C).

In examples, when first insertion needle 132 is in the first undeployed position wherein first needle distal end 198 is within first channel 186 (FIG. 5A)), insertion device 100 may be configured to fluidly isolate first medical device 120 (e.g., the fluid delivery cannula) and first insertion needle 132. For example, insertion device 100 may be configured to fluidly isolate first insertion needle 132 and first medical device 120 using a first septum 228 (FIG. 4). First septum 228 may define a portion of first conduit 156. Insertion device 100 may be configured such that, as first insertion needle 132 extends in the distal direction D1, insertion needle 132 (e.g., first distal end 198) punctures first septum 228 prior to engaging first medical device 120. First septum 228 may be comprised of a self-sealing material, such that first septum 228 substantially closes around first insertion needle 132 to substantially maintain a fluid isolation between first conduit 156 and other components of insertion device 100, such as driver 150, first linkage assembly 142, second linkage assembly 144, processor 166 including processing circuitry, memory element 168, and other portions of insertion device 100 which may be adversely impacted by contact with a fluid within first conduit 156.

First insertion needle 132 may be configured to engage first medical device 120 to cause first medical device 120 to translate in the first distal direction D1. First insertion needle 132 may be configured to exert a force on first medical device 120 in the distal direction D1 to cause the translation of first medical device 120. For example, first insertion needle 132 and/or first medical device 120 may include a first structural feature configured to cause first insertion needle 132 to exert the force in the distal direction D1 on first medical device 120 when first insertion needle 132 extends in the first distal direction D1. In examples, first insertion needle 132 is configured to enter lumen 154 to engage first medical device 120. First insertion needle 132 may be configured to engage first medical device 120 to cause implantation of first medical device in the user as first insertion needle 132 extends in the distal direction D1 into the user. First medical device 120 (e.g., a fluid delivery cannula) may be configured to extend from device housing 102 when first insertion needle 132 causes the implantation of first medical device 120 within the user. First insertion needle 132 may be configured to disengage from (e.g., release) first medical device 120 when first insertion needle 132 is subsequently retracted in the first proximal direction P1 by insertion device 100. For example, first insertion needle 132 and/or first medical device 120 may include a structural feature (the same as the first structural feature or a different structural feature) configured to allow first insertion needle 132 to move substantially independently of first medical device 120 when insertion device 100 retracts first insertion needle 132 in the first proximal direction P1.

In examples, first insertion needle 132 is configured to substantially mate with first medical device 120 when a first insertion needle 132 exerts the force in the first distal direction D1 on first medical device 120. First insertion needle 132 may be configured such that a subsequent force in the first proximal direction P1 causes first insertion needle 132 to unmate (e.g., disengage) and move independently of first medical device 120. In examples, first insertion needle 132 includes a bearing surface configured such that, when the force in the first distal direction D1 is exerted on first insertion needle 132, the bearing surface engages a portion of first medical device 120 and transmits some portion of the force to first medical device 120, and when a force in the first proximal direction P1 is exerted in first insertion needle 132, the bearing surface displaces from first medical device 120, such that first insertion needle 132 moves independently of first medical device 120. Hence, insertion device 100 may be configured to retract first insertion needle 132 in the first proximal direction P1 independently from first medical device 120, such that first medical device 120 remains implanted as first insertion needle 132 retracts.

Insertion device 100 may be configured to retract first insertion needle 132 to the first stowage position, wherein first distal end 198 is within housing 102, 126. Insertion device 100 may retract first insertion needle 132 such that first needle distal end 198 retracts through septum 228. Septum 228 may be configured to self-seal during or once first needle distal end 198 retracts through septum 228, in order to substantially maintain fluid isolation between first conduit 156 and other components of insertion device 100, such as driver 150, first linkage assembly 142, second linkage assembly 144, processor 166 including processing circuitry, memory element 168, and other portions of insertion device 100 which may be adversely impacted by contact with a fluid within first conduit 156.

As discussed, second insertion needle 134 is configured to releasably engage second medical device 122 to cause the implantation of second medical device 122 within the user. In examples, second medical device 122 is an analyte sensor configured to monitor a physiological characteristic (e.g., a glucose level) of the user. Second insertion needle 134 and the analyte sensor may be cooperatively configured and arranged such that the second insertion needle 132 releasably carries at least a portion (e.g., a distal portion) of the analyte sensor as second insertion needle 134 is caused to extend away (e.g., in the second distal direction D2) from housing 105, 155. In some examples, second insertion needle 134 configured to at least partially surround the analyte sensor to carry the analyte sensor as second insertion needle 134 extends away from housing 102, 126. Second insertion needle 134 may be configured as a substantially hollow needle defining a void that accommodates the analyte sensor within the void. Second insertion needle 134 and/or the analyte sensor may be configured such that second insertion needle 134 mechanically engages the analyte sensor when second insertion needle 134 extends in the second distal direction D2 and disengages from the analyte sensor when second insertion needle 134 retracts in the second proximal direction P2.

Second insertion needle 134 may be configured to engage second medical device 122 to cause second medical device 122 to translate in the second distal direction DS. Second insertion needle 134 may be configured to exert a force on second medical device 122 in the second distal direction D2 to cause the translation of second medical device 122. Second insertion needle 134 and/or second medical device 122 may include a second structural feature (e.g., the void defined by second insertion needle) configured to cause second insertion needle 134 to exert the force in the second distal direction D2 on second medical device 122 when second insertion needle 134 extends in the second distal direction D2. Second insertion needle 134 may be configured to engage second medical device 122 to cause implantation of second medical device 122 in the user as second insertion needle 134 extends in the second distal direction D2 into the user. Second medical device 122 (e.g., an analyte sensor) may be configured to extend from device housing 102 when second insertion needle 134 causes the implantation of second medical device 122 within the user.

Second insertion needle 134 may be configured to disengage from (e.g., release) second medical device 122 when second insertion needle 134 is subsequently retracted in the second proximal direction P2 by insertion device 100. For example, second insertion needle 134 and/or second medical device 122 may include a structural feature (the same as the second structural feature or a different structural feature) configured to allow second insertion needle 134 to move substantially independently of second medical device 122 when insertion device 100 retracts second insertion needle 134 in the second proximal direction P2. In some examples, second insertion needle 134 is configured such that body tissue within the user engages with second medical device 122 (e.g., the analyte sensor) when second insertion needle 134 retracts, such that second medical device 122 remains implanted in the user when second insertion needle 134 is withdrawn from the user. For example, second insertion needle 134 may include a portion (e.g., a distal portion) defining a longitudinal opening, such that a portion of the analyte sensor is exposed to body tissue when second insertion needle 134 and second medical device 122 are inserted in the user. The body tissue may act to grip (e.g., frictionally engage) the exposed portion of the analyte sensor as second insertion needle 134 is retracted, such that second insertion needle 134 may be retracted into housing 102, 126 as second medical device 122 remains implanted in the user. In examples, second medical device 122 (e.g., an analyte sensor) may include one or more structural features configured to assist the frictional engagement with the body tissue. In some examples, insertion device 100 may be configured to mechanically engage second medical device 122 to hold second medical device in place (e.g., within the user) when second insertion needle 132 is retracted in the second proximal direction P2.

In examples, insertion device 100 may be configured to fluidly isolate portions of insertion device 100 from second hole 116 defined by device housing 102 in order to, for example, fluidly isolate portions of insertion device 100 from the user. The portions of insertion device 100 may include driver 150, first linkage assembly 142, second linkage assembly 144, processor 166 including processing circuitry, memory element 168, and others portions of insertion device 100 which may be adversely impacted by contact with a fluid from the user. In examples, insertion device 100 includes second septum 230 (FIG. 4) configured to fluidly isolate the portions of insertion device 100 and the second hole 116. Insertion device 100 may be configured such that, as second insertion needle 134 extends in the second distal direction D2, second insertion needle 134 (e.g., second needle distal end 210) punctures second septum 230. Second septum 230 may be comprised of a self-sealing material, such that second septum 230 substantially closes around second insertion needle 134 and/or second medical device 122 to substantially maintain a fluid isolation between the portions of insertion device 100 and the user.

Insertion device 100 may be configured to retract second insertion needle 134 to the second stowage position, wherein second distal end 210 is within housing 102, 126. Insertion device 100 may retract second insertion needle 134 such that second needle distal end 210 retracts through second septum 230. Second septum 230 may be configured to self-seal (e.g., around second medical device 122) during or once second needle distal end 210 retracts through second septum 230, in order to substantially maintain fluid isolation between the components of insertion device 100 and the user.

Second medical device 122 may be fabricated using a flexible or pliable substrate or carrier. In examples, second medical device 122 (e.g., an analyte sensor) is initially provided in a folded, serpentine, coiled, or accordion shape to, for example, provide a desired amount of slack to accommodate extension of second medical device 122 while second medical device 122 is electrically coupled to insertion device 100 (e.g., to electronic assembly 172 (FIG. 4). Second medical device 122 may be configured such that, as second insertion needle 134 carries second medical device 122 in the second distal direction D2, second medical device 122 extends without losing electrical contact with the electronics assembly 172. In some examples, second medical device 122 is configured to establish electrical coupling (e.g., with electronics assembly 172) after insertion mechanism unit 124, 212 has been triggered. For example, second medical device 122 may include electrical contact pads configured to electrically connect with a one or more connectors of insertion device 100 as or when second insertion needle 132 implants second medical device 122 within the user. The one or more connectors may be, for example, one or more pogo pins or other electrical connector in electrical communication with electronics assembly 172.

Figure 7:
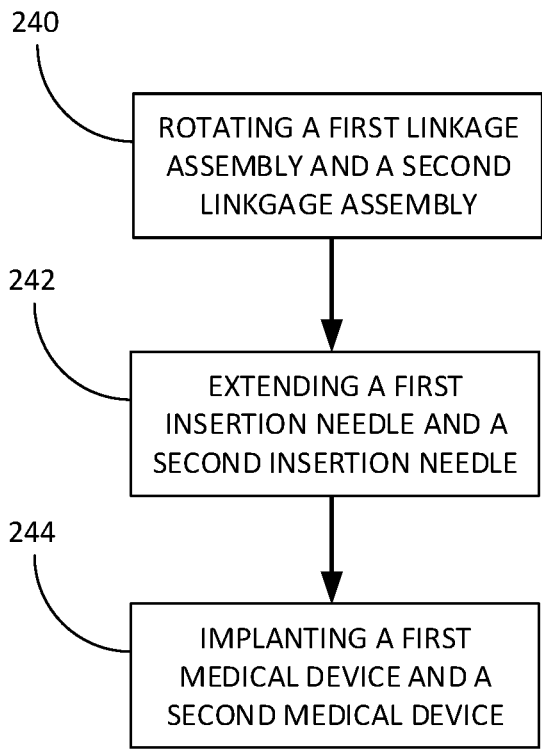
FIG. 7 illustrates an example technique of using a medical system.

A technique for implanting a first medical device and a second medical device is illustrated in FIG. 7. Although the technique is described mainly with reference to insertion device 100 of FIG. 1 through FIG. 6C, the technique may be applied to other medical systems in other examples.

The technique includes contacting a housing 102, 126 of a insertion device 100 with the skin 118 of a user. The technique includes rotating a first linkage assembly 142, 216 and a second linkage assembly 144, 220 with respect to housing 102, 126 using a driver 150, 214 (240). The technique may include rotating first assembly 142, 216 using a first torque T1. The technique may include rotating second assembly 144, 220 using a second torque T2. In examples, driver 150 includes a spring 174. The technique may include exerting first torque T1 on first linkage assembly 142, 216 using spring 174. The technique may include exerting second torque T2 on second linkage assembly 144, 220 using spring 174. In some examples, first torque T1 and second torque T2 have different rotational directions with respect to a central axis C defined by housing 102, 126. In some examples, first torque T1 and second torque T2 have the same rotational direction with respect to central axis C defined by housing 102, 126.

In examples, first linkage assembly 142, 216 includes a first input link 146, 218 rotatably connected to housing 102, 126. In examples, second linkage assembly 144, 220 includes a second input link 148, 222 rotatably connected to housing 102, 126. The technique may include rotating first input link 146, 218 using first torque T1 and rotating second input link 148, 222 using second torque T2.

The technique includes extending a first insertion needle 132 using the rotation of first linkage assembly 142, 216 and extending a second insertion needle 134 using the rotation of the second linkage assembly 144, 220 (242). The technique may include extending the first insertion needle 132 and second insertion needle 134 in a direction away from housing 102, 126. In examples, the technique includes extending first insertion needle 132 in a first direction away from housing 102, 126 and extending second insertion needle 134 in a second direction away from housing 102, 126, where the first direction is different from the second direction.

The technique may include implanting a first medical device 120 in the user using the extension of first needle 132, and implanting a second medical device 122 in the user using the extension of second insertion needle 134 (244). In examples, first medical device 120 is a fluid delivery cannula configured to the delivery of a medical fluid (e.g., insulin). In examples, second medical device 122 is an analyte sensor (e.g., a glucose sensor) configured to sense a physiological characteristic of the user (e.g., a glucose level). In examples, insertion device 100 is configured to cause the implantations such that first medical device 120 and second medical device 122 are separated by a displacement D when implanted in the user.

The technique may include extending first insertion needle 132 using a motion of a first output link 184 defining a first kinematic chain with first input link 146, 218. In examples, first output link 184 is configured to linearly translate when driver 150, 214 causes the rotation of first input link 146, 218. First output link 184 may be configured to linearly translate within a first channel 186 defined by housing 102, 126. In examples, first linkage assembly 142, 216 includes one or more floating links in the first kinematic chain between first input link 146, 218 and first output link 184. In examples, first linkage assembly 142, 216 includes a first medial link 188 rotatably coupled to first input link 146, 234 and first output link 184.

The technique may include extending second insertion needle 134 using a motion of a second output link 204 defining a second kinematic chain with second input link 148, 222. In examples, second output link 204 is configured to linearly translate when driver 150, 214 causes the rotation of second input link 148, 222. Second output link 204 may be configured to linearly translate within a second channel 208 defined by housing 102, 126. In examples, second linkage assembly 144, 220 includes one or more floating links in the second kinematic chain between second input link 148, 222 and second output link 204. In examples, second linkage assembly 144, 220 includes a second medial link 206 rotatably coupled to second input link 148, 222 and second output link 204.

The technique includes retracting first insertion needle 132 toward housing 102, 126 to withdraw first insertion needle 132 from the user using the rotation of first linkage assembly 142, 216. In examples, the technique includes causing first insertion needle 132 to release first medical device 120 when first insertion needle 132 retracts toward housing 102, 126. In examples, the technique includes retracting first insertion needle 132 using first output link 184. The technique may include reversing a direction of the linear movement of first output link 184 to cause the retraction of first insertion needle 132 toward housing 102, 126. The technique may include mechanically disengaging first insertion needle 132 from first medical device 120 such that first medical device 120 remains implanted in the user when first insertion needle 132 retracts toward housing 102, 126. The technique may include causing first insertion needle 132 to move independently of first medical device 120 during the retraction of first insertion needle 132 such that first medical device 120 remains implanted in the user when first insertion needle 132 retracts toward housing 102, 126.

The technique includes retracting second insertion needle 134 toward housing 102, 126 to withdraw second insertion needle 134 from the user using the rotation of second linkage assembly 144, 220. In examples, the technique includes causing second insertion needle 134 to release second medical device 122 when second insertion needle 134 retracts toward housing 102, 126. In examples, the technique includes retracting second insertion needle 134 using second output link 204. The technique may include reversing a direction of the linear movement of second output link 204 to cause the retraction of second insertion needle 134 toward housing 102, 126. The technique may include causing second insertion needle 134 to move independently of second medical device 122 during the retraction of second insertion needle 134 such that second medical device 122 remains implanted in the user when second insertion needle 134 retracts toward housing 102, 126.

In examples, the technique includes actuating driver 150, 214 using user input device 108 to cause the implantation of first medical device 120 and second medical device 122. In examples, user input device 108 is configured to cause driver 150, 214 to exert first torque T1 on first linkage assembly 142, 216 and exert second torque T2 on second linkage assembly 144, 220. In some examples, the technique includes depressing a button on housing 102, 126 to cause user input device 108 to initiate the implantation of first medical device 120 and second medical device 122. In some examples, the technique includes transmitting an electrical communication to user interface 112 (e.g., a wired or wireless communication) to initiate the implantation of first medical device 120 and second medical device 122.

Mechanism housing 126 may be configured to support at least driver 150, 214, first linkage assembly 142, 216, second linkage assembly 144, 220, first insertion needle 132, and second insertion needle 134. Mechanism housing 126 may be configured to engage (e.g., mechanically engage) device housing 102 of insertion device 100. The technique may include positioning at least first insertion needle 132 and second insertion needle 134 proximate the skin 118 of the user by engaging mechanism housing 126 and housing 102. The technique may include separating mechanism housing 126 and device housing 102 when first medical device 120 and second medical device 122 are implanted within the user.

The techniques and functionalities described in this disclosure, including those attributed to processor 166, processing circuitry, sensors, and/or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in any suitable device. Processing circuitry, control circuitry, and sensing circuitry, as well as other processors, controllers, and sensors described herein, may be implemented at least in part as, or include, one or more executable applications, application modules, libraries, classes, methods, objects, routines, subroutines, firmware, and/or embedded code, for example. In addition, analog circuits, components and circuit elements may be employed to construct one, some or all of the control circuitry and sensors, instead of or in addition to the partially or wholly digital hardware and/or software described herein. Accordingly, analog or digital hardware may be employed, or a combination of the two.

In one or more examples, the techniques and functionalities described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements The present disclosure includes the following examples.

Example 1: An insertion device for insertion of a first medical device and a second medical device into a user, the insertion device comprising: a housing; a first insertion needle configured to pierce and withdraw from skin of the user, the first insertion needle configured to releasably carry the first medical device; a second insertion needle configured to pierce and withdraw from the skin, the second insertion needle configured to releasably carry the second medical device; a first linkage assembly within the housing; a second linkage assembly within the housing; and a driver within the housing configured to cause the first linkage assembly and the second linkage assembly to rotate relative to the housing, wherein the first linkage assembly is configured to cause the first insertion needle to extend in a first direction away from the housing to pierce the skin and subsequently retract toward the housing to withdraw from the skin when the driver causes the first linkage assembly to rotate relative to the housing, and wherein the second linkage assembly is configured to cause the second insertion needle to extend in a second direction away from the housing to pierce the skin and subsequently retract toward the housing to withdraw from the skin when the driver causes the second linkage assembly to rotate relative to the housing.

Example 2: The insertion device of example 1, wherein one of the first medical device or the second medical device is an analyte sensor and the other of the first medical device or the second medical device is a fluid delivery cannula.

Example 3: The insertion device of example 1 or 2, wherein the first insertion needle is configured to release the first medical device within the user when the first insertion needle retracts toward the housing and the second insertion needle is configured to release the second medical device within the user when the second insertion needle retracts toward the housing.

Example 4: The insertion device of any of examples 1-3, wherein at least one of the first linkage assembly or the second linkage assembly includes an input link mechanically engaged with the driver and an output link mechanically engaged with one of the first insertion needle or the second insertion needle, wherein the input link and the output link define a kinematic chain, wherein the driver is configured to cause the input link to rotate relative to the housing, and wherein the rotation of the input link causes the output link to extend the first insertion needle in the first direction away from the housing and subsequently retract toward the housing or extend the second insertion needle in the second direction away from the housing and subsequently retract toward the housing.

Example 5: The insertion device of example 4, wherein the output link is a sliding member, and wherein the sliding member is configured to linearly translate when the driver causes the input link to rotate relative to the housing.

Example 6: The insertion device of example 4 or 5, further comprising a medial link between the input link and the output link, wherein a first end of the medial link is coupled to the input link by a first rotatable joint and a second end of the medial link is coupled to the output link by a second rotatable joint.

Example 7: The insertion device of any of examples 1-6, wherein: the first insertion needle is configured to at least partially insert within a lumen defined by the first medical device when the first insertion needle extends in the first direction away from the housing, and the second insertion needle is configured to at least partially surround the second medical device when the first insertion needle extends in the first direction away from the housing.

Example 8: The insertion device of any of examples 1-7, wherein the first linkage assembly is configured to cause the first insertion needle to pierce the skin substantially concurrently with the second linkage assembly causing the second insertion needle to pierce the skin.

Example 9: The insertion device of any of examples 1-8, further comprising: a release mechanism unit configured to establish at least a first configuration and a second configuration, wherein in the first configuration, the release mechanism unit is configured to constrain the driver from causing at least one of the first linkage assembly or the second linkage assembly to rotate relative to the housing, and wherein in the second configuration, the release mechanism unit is configured to allow the driver to cause at least one of the first linkage assembly or the second linkage assembly to rotate relative to the housing; and a user input device configured to cause the release mechanism unit to transition from the first configuration to the second configuration.

Example 10: The insertion device of any of examples 1-9, further comprising: a fluid pump; a fluid reservoir, wherein the fluid pump is configured to deliver a fluid from a fluid reservoir to the first medical device; and processing circuitry, wherein the processing circuitry is configured to receive a signal indicative of a physiological characteristic of the user from the second medical device.

Example 11: The insertion device of any of examples 1-10, wherein the first insertion needle is configured to extend in the first direction to pierce the skin at a first location and the second insertion needle is configured to extend in the second direction to pierce the skin at a second location displaced from the first location.

Example 12: The insertion device of any of examples 1-11, wherein the housing defines a central axis, and wherein the driver is configured to impart a first torque around the central axis on the first linkage assembly and a second torque around the central axis on the second linkage assembly to cause the first linkage assembly and the second linkage assembly to rotate relative to the housing.

Example 13: The insertion device of any of examples 1-12, wherein the driver includes a spring configured to cause the driver to impart a first torque on the first linkage assembly and a second torque on the second linkage assembly.

Example 14: The insertion device of any of examples 1-13, wherein the housing is a mechanism housing mechanically engaged with the driver, and further comprising a device housing, wherein: the device housing is configured to contact the skin of the user, the mechanism housing is configured to mechanically engage the device housing to position the mechanism housing proximate the skin of the user, and the mechanism housing is configured to detach from the device housing.

Example 15: An insertion device for insertion of a first medical device and a second medical device into a user, the insertion device comprising: a housing; a first insertion needle configured to pierce and withdraw from skin of the user at a first location, the first insertion needle configured to releasably carry the first medical device; a second insertion needle configured to pierce and withdraw from skin of the user at a second location displaced from the first location, the second insertion needle configured to releasably carry the second medical device; a first linkage assembly within the housing; a second linkage assembly within the housing; and a driver configured to cause the first linkage assembly and the second linkage assembly to rotate relative to the housing, wherein: the first linkage assembly is configured to cause the first insertion needle to extend in a first direction away from the housing to pierce the skin and subsequently retract toward the housing to withdraw from the skin when the first linkage rotates relative to the housing, the first insertion needle is configured to release the first medical device when the first insertion needle retracts toward the housing, the second linkage assembly is configured to cause the second insertion needle to extend in a second direction away from the housing to pierce the skin and subsequently retract toward the housing to withdraw from the skin when the second linkage rotates relative to the housing, and the second insertion needle is configured to release the second medical device when the second insertion needle retracts toward the housing.

Example 16: The insertion device of example 15, further comprising: a fluid pump; a fluid reservoir, wherein the fluid pump is configured to deliver a fluid from a fluid reservoir to the first medical device; and processing circuitry, wherein the processing circuitry is configured to receive a signal indicative of a physiological characteristic of the user from the second medical device.

Example 17: The insertion device of example 15 or 16, wherein the driver includes a spring configured to cause the driver to impart a first torque on the first linkage assembly and a second torque on the second linkage assembly.

Example 18: The insertion device of any of examples 15-17, wherein at least one of the first linkage assembly or the second linkage assembly include an input link mechanically engaged with the driver and an output link mechanically engaged with one of the first insertion needle or the second insertion needle, wherein the input link and the output link define a kinematic chain, wherein the driver is configured to cause the input link to rotate relative to the housing, and wherein the rotation of the input link causes the output link to extend the first insertion needle in the first direction away from the housing and subsequently retract toward the housing or extend the second insertion needle in the second direction away from the housing and subsequently retract toward the housing.

Example 19: A method comprising: extending a first insertion needle of the insertion device in a first direction away from a housing to pierce skin using rotation of a first linkage assembly with respect to the housing, wherein the first insertion needle is configured to releasably carry a first medical device; extending a second insertion needle of the insertion device in a second direction away from the housing to pierce the skin using rotation of a second linkage assembly with respect to the housing, wherein the second insertion needle is configured to releasably carry a second medical device; retracting the first insertion needle toward the housing to withdraw from the skin using the rotation of the first linkage assembly; and retracting the second insertion needle toward the housing to withdraw from the skin using the rotation of the second linkage assembly.

Example 20: The method of example 20, further comprising: positioning the first medical device in the user by releasing the first medical device from the first insertion needle when the first insertion needle retracts toward the housing; and positioning the second medical device in the user by releasing the second medical device from the second insertion needle when the second insertion needle retracts toward the housing.

Various examples have been described. These are other examples are within the scope of the disclosure.

We claim:

1. An insertion device for insertion of a first medical device and a second medical device into a user, the insertion device comprising:

a housing;

a first insertion needle configured to pierce and withdraw from skin of the user, the first insertion needle configured to releasably carry the first medical device;

a second insertion needle configured to pierce and withdraw from the skin, the second insertion needle configured to releasably carry the second medical device;

a first linkage assembly within the housing and comprising a first input link;

a second linkage assembly within the housing and comprising a second input link; and a driver within the housing configured to cause the first input link and the second input link to rotate around the same axis of rotation relative to the housing, wherein the first linkage assembly is configured to cause the first insertion needle to extend in a first direction away from the housing to pierce the skin and subsequently retract toward the housing to withdraw from the skin when the driver causes the first input link to rotate relative to the housing, and wherein the second linkage assembly is configured to cause the second insertion needle to extend in a second direction away from the housing to pierce the skin and subsequently retract toward the housing to withdraw from the skin when the driver causes the second input link to rotate relative to the housing.

2. The insertion device of claim 1, wherein at least one of the first input link and the second input link is configured to rotate without translating relative to the housing.

3. The insertion device of claim 1, wherein the driver and at least one of the first input link and the second input link are configured to not rotate relative to each other.

4. The insertion device of claim 1, wherein at least one of the first linkage assembly and the second linkage assembly comprises:

an output link coupled to the first insertion needle or the second insertion needle; and a medial link rotatably coupled to the output link and rotatably coupled to the first input link or the second input link.

5. The insertion device of claim 1, wherein the first linkage assembly is configured to cause the first insertion needle to pierce the skin substantially concurrently with the second linkage assembly causing the second insertion needle to pierce the skin.

6. The insertion device of claim 1, wherein the first insertion needle is configured to release the first medical device within the user when the first insertion needle retracts toward the housing and the second insertion needle is configured to release the second medical device within the user when the second insertion needle retracts toward the housing.

7. The insertion device of claim 1, wherein one of the first medical device or the second medical device is an analyte sensor and the other of the first medical device or the second medical device is a fluid delivery cannula.

8. The insertion device of claim 1, further comprising:

a release mechanism unit configured to establish at least a first configuration and a second configuration, wherein in the first configuration, the release mechanism unit is configured to constrain the driver from causing at least one of the first input link and the second input link to rotate relative to the housing, and wherein in the second configuration, the release mechanism unit is configured to allow the driver to cause at least one of the first input link and the second input link to rotate relative to the housing.

9. An insertion device for insertion of a first medical device and a second medical device into a user, the insertion device comprising:

a housing;

a first insertion needle configured to pierce and withdraw from skin of the user, the first insertion needle configured to releasably carry the first medical device;

a second insertion needle configured to pierce and withdraw from the skin, the second insertion needle configured to releasably carry the second medical device;

a first linkage assembly within the housing;

a second linkage assembly within the housing; and a driver within the housing configured to cause the first linkage assembly and the second linkage assembly to rotate relative to the housing, wherein the first linkage assembly is configured to cause the first insertion needle to extend in a first direction away from the housing to pierce the skin and subsequently retract toward the housing to withdraw from the skin when the driver causes the first linkage assembly to rotate relative to the housing, wherein the second linkage assembly is configured to cause the second insertion needle to extend in a second direction away from the housing to pierce the skin and subsequently retract toward the housing to withdraw from the skin when the driver causes the second linkage assembly to rotate relative to the housing, and wherein each of the first linkage assembly and the second linkage assembly includes a respective input link directly coupled to the driver such that the respective input link is configured to rotate without translating relative to the housing.

10. The insertion device of claim 9, wherein the driver and each respective input link are configured to not rotate relative to each other.

11. The insertion device of claim 9, wherein at least one of the first linkage assembly and the second linkage assembly comprises:

an output link coupled to the first insertion needle or the second insertion needle; and a medial link rotatably coupled to the output link and rotatably coupled to the respective input link.

12. The insertion device of claim 9, wherein the first linkage assembly is configured to cause the first insertion needle to pierce the skin substantially concurrently with the second linkage assembly causing the second insertion needle to pierce the skin.

13. The insertion device of claim 9, wherein the first insertion needle is configured to release the first medical device within the user when the first insertion needle retracts toward the housing and the second insertion needle is configured to release the second medical device within the user when the second insertion needle retracts toward the housing.

14. The insertion device of claim 9, wherein one of the first medical device or the second medical device is an analyte sensor and the other of the first medical device or the second medical device is a fluid delivery cannula.

15. The insertion device of claim 9, further comprising:

a release mechanism unit configured to establish at least a first configuration and a second configuration, wherein in the first configuration, the release mechanism unit is configured to constrain the driver from causing at least one of the first linkage assembly and the second linkage assembly to rotate relative to the housing, and wherein in the second configuration, the release mechanism unit is configured to allow the driver to cause at least one of the first linkage assembly and the second linkage assembly to rotate relative to the housing.

16. An insertion device for insertion of a first medical device and a second medical device into a user, the insertion device comprising:

a housing;

a first insertion needle configured to pierce and withdraw from skin of the user, the first insertion needle configured to releasably carry the first medical device;

a second insertion needle configured to pierce and withdraw from the skin, the second insertion needle configured to releasably carry the second medical device;

a first linkage assembly within the housing;

a second linkage assembly within the housing; and a driver within the housing configured to cause the first linkage assembly and the second linkage assembly to rotate relative to the housing, wherein the first linkage assembly is configured to cause the first insertion needle to extend in a first direction away from the housing to pierce the skin and subsequently retract toward the housing to withdraw from the skin when the driver causes the first linkage assembly to rotate relative to the housing, wherein the second linkage assembly is configured to cause the second insertion needle to extend in a second direction away from the housing to pierce the skin and subsequently retract toward the housing to withdraw from the skin when the driver causes the second linkage assembly to rotate relative to the housing, and wherein each of the first linkage assembly and the second linkage assembly comprises a respective input link coupled to the driver such that the driver and the respective input link are configured to not rotate relative to each other.

17. The insertion device of claim 16, wherein at least one of the first linkage assembly and the second linkage assembly comprises:

an output link coupled to the first insertion needle or the second insertion needle; and a medial link rotatably coupled to the output link and rotatably coupled to the respective input link.

18. The insertion device of claim 16, wherein the first linkage assembly is configured to cause the first insertion needle to pierce the skin substantially concurrently with the second linkage assembly causing the second insertion needle to pierce the skin.

19. The insertion device of claim 16, wherein one of the first medical device or the second medical device is an analyte sensor and the other of the first medical device or the second medical device is a fluid delivery cannula.

20. The insertion device of claim 16, further comprising:

a release mechanism unit configured to establish at least a first configuration and a second configuration, wherein in the first configuration, the release mechanism unit is configured to constrain the driver from causing at least one of the first linkage assembly and the second linkage assembly to rotate relative to the housing, and wherein in the second configuration, the release mechanism unit is configured to allow the driver to cause at least one of the first linkage assembly and the second linkage assembly to rotate relative to the housing.

\* \* \* \* \*